United States Patent
Si et al.

(10) Patent No.: US 12,071,702 B2
(45) Date of Patent: Aug. 27, 2024

(54) ACIDIC AQUEOUS COMPOSITION FOR ELECTROLYTIC COPPER PLATING

(71) Applicant: Atotech Deutschland GmbH, Berlin (DE)

(72) Inventors: Kun Si, Berlin (DE); Ralf Schmidt, Berlin (DE); Onas Bolton, Berlin (DE); Josef Gaida, Berlin (DE); Frank Von Horsten, Berlin (DE); Dirk Rohde, Berlin (DE); Himendra Jha, Berlin (DE); Jens Palm, Berlin (DE); Olivier Mann, Berlin (DE); Angela Llavona-Serrano, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 687 days.

(21) Appl. No.: 17/315,810

(22) Filed: May 10, 2021

(65) Prior Publication Data
US 2021/0262105 A1    Aug. 26, 2021

Related U.S. Application Data

(62) Division of application No. 16/323,582, filed as application No. PCT/EP2017/070286 on Aug. 10, 2017, now Pat. No. 11,035,051.

(30) Foreign Application Priority Data

Aug. 15, 2016 (EP) ..................... 16184200

(51) Int. Cl.
| | | |
|---|---|---|
| *C07C 215/20* | (2006.01) | |
| *C07C 215/24* | (2006.01) | |
| *C07D 215/20* | (2006.01) | |
| *C07D 215/24* | (2006.01) | |
| *C25D 3/38* | (2006.01) | |
| *C25D 5/18* | (2006.01) | |
| *C25D 7/12* | (2006.01) | |

(52) U.S. Cl.
CPC .............. *C25D 3/38* (2013.01); *C07C 215/20* (2013.01); *C07C 215/24* (2013.01); *C07D 215/20* (2013.01); *C07D 215/24* (2013.01); *C25D 5/18* (2013.01); *C25D 7/123* (2013.01)

(58) Field of Classification Search
USPC ....................................... 528/422
See application file for complete search history.

(56) References Cited

U.S. PATENT DOCUMENTS

| 4,009,087 | A | 2/1977 | Kardos et al. |
|---|---|---|---|
| 4,374,709 | A | 2/1983 | Combs |
| 4,385,967 | A | 5/1983 | Brady et al. |
| 4,496,436 | A | 1/1985 | Inoue |
| 4,776,939 | A | 10/1988 | Blasing et al. |
| 5,976,341 | A | 11/1999 | Schumacher et al. |
| 6,099,711 | A | 8/2000 | Dahms et al. |
| 8,679,316 | B2 | 3/2014 | Brunner et al. |
| 9,506,158 | B2 | 11/2016 | Rohde et al. |
| 9,551,080 | B2 | 1/2017 | Brunner et al. |
| 9,598,787 | B2 | 3/2017 | Jayaraju et al. |
| 2002/0036144 | A1 | 3/2002 | Lee et al. |
| 2005/0247577 | A1 | 11/2005 | Pavlov et al. |
| 2014/0262799 | A1 | 9/2014 | Jayaraju et al. |

FOREIGN PATENT DOCUMENTS

| CA | 2093924 | | 4/1992 |
|---|---|---|---|
| CN | 101362719 A | | 2/2009 |
| CN | 102250101 A | * | 11/2011 |
| CN | 102952070 A | | 3/2013 |
| DE | 4225961 | | 2/1994 |
| JP | 2000026994 | | 1/2000 |
| JP | 2004137530 | | 5/2004 |
| JP | 2005256120 | | 9/2005 |

OTHER PUBLICATIONS

CN-102250101-A Machine Translation (Year: 2011).*
PCT/EP2017/070286; PCT International Search Report and Written Opinion of the International Searching Authority dated Aug. 23, 2017.

* cited by examiner

*Primary Examiner* — Terressa Boykin
(74) *Attorney, Agent, or Firm* — Renner, Otto, Boisselle & Sklar, LLP

(57) ABSTRACT

The present invention relates to a composition comprising one or a mixture of two or more quinoline-polyethylene glycol containing compound, each quinoline-polyethylene glycol containing compound comprising:
  one to three quinoline group and
  one or more polyethylene glycol group,
wherein, in each said quinoline-polyethylene glycol containing compound, one to three of said one to three quinoline group is connected via one or more oxygen atom of said one or more polyethylene glycol group via carbon 6 or carbon 8 of said one to three quinoline group.

2 Claims, 5 Drawing Sheets

ACIDIC AQUEOUS COMPOSITION FOR ELECTROLYTIC COPPER PLATING

RELATED APPLICATIONS

The present application is a division of and claims priority under 35 U.S.C. § 120 to U.S. application Ser. No. 16/323,582, filed 6 Feb. 2019, now U.S. Pat. No. 11,035,051 B2, which is a U.S. National Stage Application based on and claiming benefit and priority under 35 U.S.C. § 371 of International Application No. PCT/EP2017/070286, filed 10 Aug. 2017, which in turn claims benefit of and priority to European Application No. 16184200.0 filed 15 Aug. 2016, the entireties of all of which are hereby incorporated herein by reference.

FIELD OF THE INVENTION

The present invention relates to an acidic aqueous composition (plating bath) for electrolytic copper plating (electrolytic deposition of copper), the composition comprising
(i) copper (II) ions,
(ii) one or more than one compound of Formula (Ia)

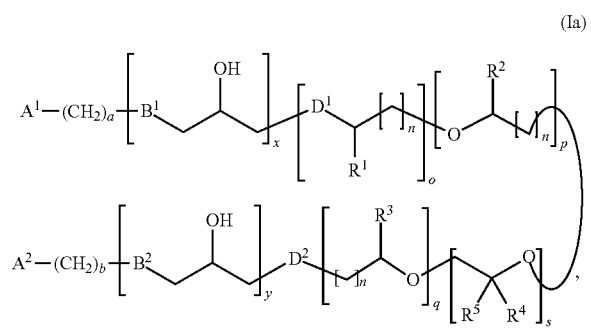

(iii) one, two, three or more than three further compounds, which are different from the compound of Formula (Ia), with the definitions given below, the use of the acidic aqueous composition according to the invention for electrolytic copper plating, the use of the compound of Formula (Ia) in an acidic aqueous composition for electrolytic metal plating, a method of electrolytic copper plating using the acidic aqueous composition according to the invention, and specific compounds derived from Formula (Ia) for an acidic aqueous composition for electrolytic metal plating.

The acidic aqueous composition according to the present invention is suitable in the electrolytic deposition of copper, in particular for filling blind micro vias (BMVs), through vias, trenches and similar structures. Thus, the method of the present invention is suitable in the manufacture of printed circuit boards (PCB), integrated circuit (IC) substrates and the like as well as for metallization of semiconducting and glass substrates.

BACKGROUND OF THE INVENTION

Acidic aqueous compositions (aqueous acidic plating baths) for electrolytic copper plating (electrolytic deposition of copper) are used for manufacturing printed circuit boards (PCB) and IC substrates where fine structures like trenches, through holes (TH), blind micro vias (BMV) and pillar bumps need to be filled or build up with copper. Another application of such compositions is filling of recessed structures such as through silicon vias (TSV) and dual damascene (DD) plating or forming redistribution layers (RDL) and pillar bumps in and on semiconducting substrates. Still another application which is becoming more demanding is filling through glass vias, i.e. holes and related recessed structures in glass substrates with copper (or copper alloys) by electroplating.

With the progressive miniaturization of printed circuit boards, design and complexity are constantly increasing. It is typically the aim to increase the calculating capacity and/or functionality in an ever decreasing space. Along with it, the geometry, for example of the printed circuit boards or of the conductor structures on printed circuit boards, chip carriers and semiconductor wafers is becoming more and more complex and complicated. For example, the ratio of the copper thickness to the width of a conductor path or respectively of the hole depth relative to the diameter of the hole (aspect ratio) is constantly becoming greater as the hole diameters are becoming smaller and smaller and the conductor paths narrower and narrower.

It is generally accepted that structures exhibiting a comparatively high aspect ratio (e.g. 6:1 to 3:1) demand a sophisticated method of electrolytic copper plating because such structures exhibit a variable electric depositing behavior. In particular, it has been shown in our own experiments that the formation of uniform and reliable conductor structures in trenches and vias on printed circuit boards, using methods known in the art, is in many cases insufficient and often very difficult. For example, due to the comparatively increased aspect ratio of structures (and, thus, the variable electric depositing behavior), a copper layer with an uneven surface is often formed as the copper is being deposited. An uneven surface, however, often results in additional challenges during chemical/mechanical polishing after the deposition of copper. It is typically a prerequisite for respective polishing steps that the copper surfaces generated during the electrolytic deposition process are extensively smooth and even so that metal can be removed in a reliable manner up to the desired depth. Furthermore, a smooth and even surface contributes to a high level of reproducibility.

Adding numerous different organic additives to aqueous compositions for electrolytic copper plating in order to enable the decorative and functional characteristics of the copper coatings to be controlled is well known. Typically, two types of additives are used in acidic aqueous compositions for electrolytic copper plating.

First, a "suppressor" (also known as "carrier"), which "is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating [ . . . ]" (see US 2005/0247577 A1, paragraph) [0007].

Second, an anti-suppressor (also known as "brightener" or "accelerator"), having the purpose "to counter the suppressive effect of the suppressor and provide the accelerated deposition within substrate recesses needed for leveling" (see again US 2005/0247577 A1, paragraph [0007]).

In order to obtain properly copper filled structures, a third organic additive is typically used, a "leveler" (also known as "booster"). A "leveler" "is typically an organic compound containing nitrogen or oxygen that also tends to decrease the copper plating rate" (see US 2005/0247577 A1, paragraph [0009]).

The above mentioned additives often positively affect the uniform deposition and metallization of copper during the plating process. It has been shown that in very small structures that are to be completely filled by copper such additives usually help avoiding the formation of hollow spaces (voids) in the copper deposit.

Unfortunately, in some cases organic additives are co-deposited along with metal ions (e.g. copper ions) assuming that undesired effects such as increased electromigration result. It is generally assumed that the co-deposition of such additives is increased if the adhesion of said additives towards the plating surface is very strong. Thus, there is a demand for additives exhibiting proper adhesion properties.

Furthermore, it is basically assumed that the copper filling quality of structures exhibiting a comparatively high aspect ratio (e.g. 6:1 to 3:1) correlates with the overpotential generated in a respective acidic aqueous composition for electrolytic copper plating (*J. Electrochem. Soc.* 2004, 151, C702-C711).

There is an ongoing demand to provide new and improved acidic aqueous compositions for electrolytic copper plating (and respective plating methods) in order to obtain uniform and void-free copper deposits, wherein the deposits contain comparatively low amounts of organic additives. Furthermore, respective compositions should exhibit an adequate stability (shelf life).

EP 2 778 260 A2 discloses methods of filling through-holes. The disclosed methods inhibit or reduce dimpling and voids during copper electroplating of through holes with flash copper layers in substrates such as printed circuit boards. EP 2 778 260 A2 discloses an aqueous acid solution consisting essentially of one or more inorganic acids and one or more reaction products of one or more aromatic heterocyclic nitrogen compounds and one or more epoxy-containing compounds, the one or more reaction products are in amounts of 1 ppm to 50 ppm.

U.S. Pat. No. 4,009,087 A relates to a process and to novel compositions for electrodepositing copper from an aqueous acidic copper plating bath. The bath contains at least one member independently selected from each of the two groups (i) an N-heteroaromatic compound containing 1 or 2 N-heteroaromatic rings and sulfoalkyl sulfide and sulfoaryl sulfide compounds.

JP 2004-137530 A relates to a composite alloy metal sphere as connector of electrical/electronic circuit components. The metal sphere surfaces are provided with electroplated silver-copper alloy film layers. JP'530 discloses a respective plating bath.

JP 2000-026994 A relates to electric-electronic circuit parts comprising a lead-free tin-copper alloy plating film as solder. JP'994 discloses a respective plating bath.

Objective of the Present Invention

It is the objective of the present invention to provide an acidic aqueous composition (plating bath) for electrolytic copper plating (electrolytic deposition of copper) exhibiting good plating qualities (i.e. basically free of voids and obtaining a uniform deposition of copper) during the electrolytic plating process, in particular for a substrate with structures exhibiting both low and high aspect ratios. It was an additional objective to provide an acidic aqueous composition that exhibits an increased overpotential compared to a composition comprising typically polyethylene glycol (PEG) as suppressor additive. It is furthermore desired that such compositions exhibit an adequate stability (shelf life) and lead to copper deposits containing comparatively low amounts of organic additives, i.e. exhibit an adequate adhesion on the copper surface.

It is furthermore an objective of the present invention to provide a respective method for electrolytic copper plating (electrolytic deposition of copper), which allows a comparatively fast copper filling of structures exhibiting low and high aspect ratios on the one hand and an adequate plating quality on the other hand.

SUMMARY OF THE INVENTION

The objectives mentioned above are solved by an acidic aqueous composition for electrolytic copper plating, the composition comprising
(i) copper (II) ions,
(ii) one or more than one compound of Formula (Ia)

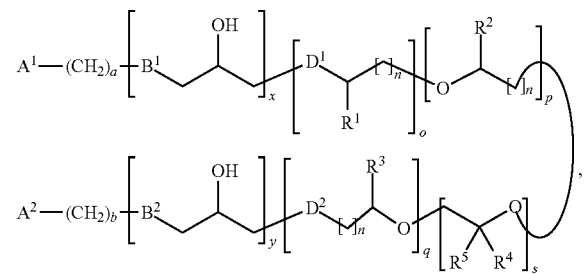

wherein
$R^4$ and $R^5$ are independently selected from the group consisting of hydrogen, methyl, ethyl, linear C3 to C16 alkyl, branched C3 to C16 alkyl and a moiety of Formula (IIa)

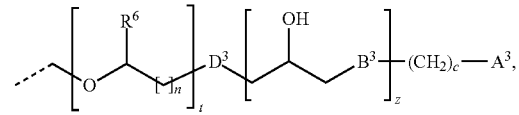

$R^1$, $R^2$, $R^3$ and $R^6$ are independently selected from the group consisting of hydrogen, methyl and ethyl, $B^1$, $B^2$, $B^3$, $D^1$, $D^2$, and $D^3$ are independently selected from the group consisting of O and NH, $A^1$, $A^2$ and $A^3$ independently denote a moiety selected from the group consisting of
  hydrogen, methyl, ethyl, linear C3 to C16 alkyl and branched C3 to C16 alkyl,

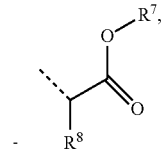

wherein $R^7$ and $R^8$ are independently selected from the group consisting of hydrogen, methyl, ethyl, linear C3 to C10 alkyl and branched C3 to C10 alkyl, and

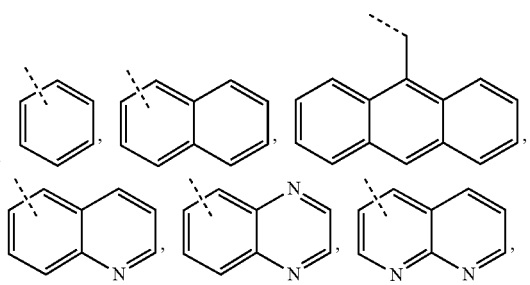

with the proviso that
at least one of $A^1$, $A^2$ and $A^3$ is a moiety selected from the group consisting of

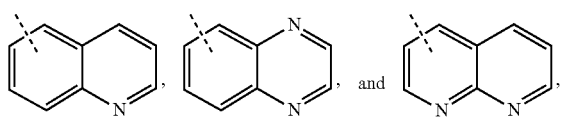

and
the corresponding $B^1$, $B^2$, and $B^3$ of the at least one of $A^1$, $A^2$ and $A^3$ is O (oxygen) if the corresponding x, y, and z is 1,
a, b and c are independently 0, 1, 2 or 3,
s, x, y, and z are independently 0 or 1,
n independently is 1, 2 or 3,
o+p+q+t=5 to 300,
and
(iii) one, two, three or more than three further compounds, which are different from the compound of Formula (Ia).

Furthermore, the objectives are solved by a method of electrolytic copper plating, comprising the steps
(a) providing or manufacturing a substrate suitable for electrolytic copper plating,
(b) contacting the substrate obtained after step (a), or obtained after an additional step after step (a) but before step (b), with the acidic aqueous composition according to the present invention (as defined above, preferably as defined below as being preferred) and applying an electrical current such that copper is electrolytically plated onto the substrate.

DETAILED DESCRIPTION OF THE INVENTION

Figure 1:
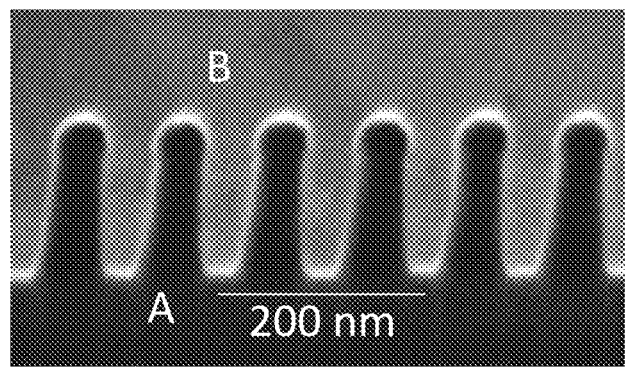
FIG. 1 shows trenches (aspect ratio approximately 4:1) in a substrate (A) filled with copper (B) (an acidic aqueous composition according to the invention comprising the compound of Formula (a) was used).

According to our own experiments (see section "Examples" below in the text), the acidic aqueous composition according to the present invention typically provided very good copper fillings (free of voids) for structures exhibiting low and high aspect ratios (see "Examples"). Furthermore, in a large number of cases the amount of organic additives in the copper deposit was significantly lower compared to acidic aqueous compositions known from the art.

Our own experiments have also shown that the acidic aqueous composition according to the present invention (as defined above) exhibits a significantly increased overpotential, compared to an acidic aqueous composition (not according to the invention) comprising polyethylene glycol instead of a compound of component (ii) (see "Examples" below).

The acidic aqueous composition according to the present invention (as defined above) is an aqueous solution. The term "aqueous solution" means that the prevailing liquid medium, which is the solvent in the composition, is water. In some cases it is preferred that the composition comprises liquids that are miscible with water. Preferred liquids are alcohols that are miscible with water. For ecological reasons, water as the sole solvent is preferred.

The acidic aqueous composition according to the invention (as defined above, preferably defined as being preferred) is typically prepared by dissolving all components and compounds (and subsequent stirring), respectively, in the aqueous liquid medium, preferably in water.

The composition according to the present invention (as defined above, preferably defined as being preferred) contains one or more than one acid, preferably selected from the group consisting of sulphuric acid, fluoroboric acid, phosphoric acid and methane sulphonic acid. The total amount of the one or more than one acid in the composition according to the present invention is preferably in a range of from 5 g/L to 400 g/L, more preferably in a range of from 10 g/L to 300 g/L, based on the total volume of the composition. If the total amount is much above 400 g/L the effect is that the bottom-up fill in the trench is insufficient. These acids are preferably counted among the one, two, three or more than three further compounds.

The pH value of the composition according to the present invention (as defined above, preferably defined as being preferred) is 3 or less, preferably 2 or less, measured at a temperature of 20° C. This means that the pH value of the composition of the present invention is 3 or less, preferably 2 or less. In the context of the present invention the pH value is determined at a temperature of 20° C., i.e. the defined pH value is referenced to 20° C. Thus, only for the sake of pH determination the composition has a temperature of 20° C. This does not mean that the composition of the present invention in itself is limited to the specific temperature of 20° C. For preferred temperatures of the composition see below.

If the pH is much above 3 the effect is that the conductivity in the composition is mostly insufficient leading to an unbalanced current density in the composition while plating. Furthermore, a pH of 3 or below prevents the formation of insoluble copper oxide. As a result, no complexing agents are needed in the composition of the present invention. Thus, preferred is an acidic aqueous composition for electrolytic copper plating according to the present invention being substantially free of (preferably does not contain) complexing agents. The absence of complexing agents is preferred because the risk to include organic additives into the copper deposit is further minimized. If no complexing agents are included in the composition of the present invention typically no significant carbon content is observed in the copper deposit. Preferably, the electrolytically plated copper obtained in the method of the present invention comprises at least 99 weight-% copper, based on the total weight of the electrolytically plated copper, more preferably at least 99.9 weight-% copper.

The acidic aqueous composition for electrolytic copper plating according to the present invention comprises copper (II) ions. Preferably, the copper ion source is selected from the group consisting of copper sulphate, copper chloride, copper nitrate, copper fluoroborate, copper acetate, copper citrate, copper phenyl sulphonate, copper para-toluene sulphonate, and copper alkyl sulphonates. A preferred copper alkyl sulphonate is copper methane sulphonate. The most preferred copper source is copper sulphate, most preferably $CuSO_4*5\ H_2O$.

Preferably, the total amount of copper sulphate ($CuSO_4*5\ H_2O$) in the acidic aqueous composition for electrolytic copper plating according to the present invention is 20 g/L to 250 g/L, preferably 30 g/L to 220 g/L, based on the total volume of the acidic aqueous composition. In some specific cases a total amount of 30 g/L to 80 g/L is preferred, wherein in other specific cases a total amount of 180 g/L to 220 g/L is preferred. Respective molar amounts per litre can be calculated by the skilled person for the total amount of copper (II) ions if sources other than $CuSO_4*5\ H_2O$ are used. In some cases a total amount of copper (II) ions (irrespective of the copper source) is preferred corresponding to the aforementioned concentrations for copper sulphate ($CuSO_4*5\ H_2O$) in g/L.

In general, in the composition according to the invention (as defined above, preferably defined as being preferred) the total amount of copper (II) ions is in the range of from 3 to 70 g/L, preferably in the range of from 5 to 70 g/L, based on the total volume of the composition.

Preferred is a composition of the present invention, wherein said copper (II) ions in the composition represent at least 95 mol-% of all depositable metal cations in the composition, more preferably at least 98 mol-%, even more preferably at least 99 mol-%, most preferably 99.9 mol-%. "Depositable metal cations" are cations that are deposited in metallic form together with copper if an electric current is applied. Such a "depositable metal cation" is for example tin, nickel and silver.

Preferred is a composition of the present invention, wherein said copper (II) ions in the composition represent at least 95 mol-% of all transition metal cations in the composition, more preferably at least 98 mol-%, even more preferably at least 99 mol-%, most preferably at least 99.9 mol-%. More preferred is a composition of the present invention, wherein said copper (II) ions in the composition represent at least 95 mol-% of all transition metal cations together with metal ions of main groups III, IV, and V of the periodic table, more preferably at least 98 mol-%, even more preferably at least 99 mol-%, most preferably at least 99.9 mol-%.

Preferably, the acidic aqueous composition of the present invention is not for a copper alloy.

Most preferred is a composition of the present invention, wherein said copper (II) ions are the only depositable metal cations. Thus, the electrolytically plated copper in the method of the present invention is most preferably pure copper. In the context of the present invention, "pure copper" denotes that the electrolytically plated copper comprises at least 99.5 weight-% copper, based on the total weight of the electrolytically plated copper.

Preferred is a composition of the present invention, wherein the composition is substantially free of (preferably does not contain) transition metals other than copper. Also preferred is a composition, wherein the composition is (preferably in addition to the aforementioned) substantially free of (preferably does not contain) aluminium, gallium, indium, tin, and lead.

In the context of the present invention, the term "substantially free" of a subject-matter (e.g. a compound, a metal ion, etc.) denotes that said subject-matter is not present at all or is present only in (to) a very little and undisturbing amount (extent) without affecting the intended purpose of the invention. For example, such a subject-matter might be added or utilized unintentionally, e.g. as unavoidable impurity. "Substantially free" preferably denotes 0 (zero) ppm to 50 ppm, based on the total weight of the composition of the present invention, if defined for said composition, or based on the total weight of the electrolytically plated copper obtained in the method of the present invention, if defined for said plated copper; preferably 0 ppm to 25 ppm, more preferably 0 ppm to 10 ppm, even more preferably 0 ppm to 5 ppm, most preferably 0 ppm to 1 ppm.

The acidic aqueous composition for electrolytic copper plating according to the present invention (as defined above, preferably defined as being preferred) comprises one or more than one compound of Formula (Ia) (as defined above and below, preferably at least one or more than one compound defined as being preferred). In some cases it is preferred that the acidic aqueous composition for electrolytic copper plating according to the present invention (as described above, preferably defined as being preferred) comprises only one compound of Formula (Ia) (as defined above and below, preferably one compound defined as being preferred).

Throughout the text the word "independently" (e.g. in terms such as "independently selected" or "independently denote(s)") is used for moieties and groups. The meaning of this word is explained by means of the following example:

For an example-compound X with example-groups E, F, and G, "E, F, and G are independently selected from a group consisting of [ . . . ]". This means that (i) example-group F in example-compound X is independently selected from example-groups E and G in the example-compound X and (ii) example-group F in example-compound X is independently selected from other example-groups F in other example-compounds, e.g. in an example-compound Y.

Throughout the text, in Formula (Ia) and Formula (Ib) a curved line is depicted between the [—$CH_2$—]$_n$-group in moiety p and the oxygen atom in moiety s. The curved line represents a covalent bond connecting the carbon atom of the $n^{th}$-$CH_2$-group in moiety p with the oxygen atom in moiety s. If p and/or s is zero the curved line represents a corresponding connecting covalent bond of the respective previous and/or next atom according to the formula.

Furthermore, if s is zero, the compound of Formula (Ia) does not comprise a $R^4$ and $R^5$ moiety. This also means that the compound of Formula (Ia) does not comprise a moiety of Formula (IIa). As a result, variables t, z, and c in a compound of Formula (IIa) are counted zero in such a case.

Throughout the text the term "alkyl" is used and refers to an univalent group derived from alkanes by removal of a hydrogen atom from any carbon atom ($C_nH_{2n+1}$). The term e.g. "C3 to C16 alkyl" refers to an alkyl group with 3 to 16 carbon atoms (n=3 to 16). Throughout the text C3 alkyl explicitly includes n-propyl and iso-propyl, C4 alkyl explicitly includes n-butyl, iso-butyl, see-butyl, tert-butyl and C5 alkyl explicitly includes

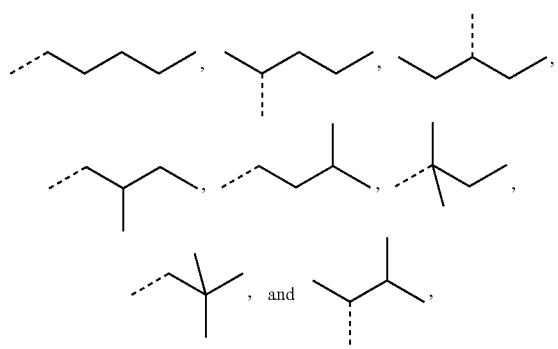

wherein the dashed line represents the covalent bond for binding the respective carbon atom of the alkyl radical with the respective atom of a molecule (connecting bond).

In some Formulae throughout the present text other dashed lines are depicted. However, such dashed lines are not connected with any of its ends to a specific carbon atom. Rather, the dashed line crosses a covalent bond. For example, some ring structures among the $A^1$-, $A^2$-, and $A^3$-moieties are depicted with such a dashed line, crossing a covalent bond. Such a dashed line represents a single covalent bond connecting a (suitable) carbon atom in the respective $A^1$-, $A^2$-, and $A^3$-moiety with the rest of the compound of Formula (Ia) and Formula (Ib), respectively. For example, $A^1$, $A^2$, and $A^3$ comprises the moiety

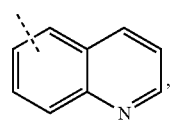

which is a quinoline moiety. The typical ring numbering in quinoline is as follows:

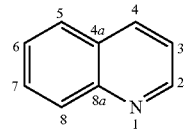

For example, in some cases this moiety is connected to the rest of the compound of Formula (Ia) and (Ib), respectively, as follows:

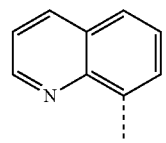

(connected via carbon 8), in other cases as follows:

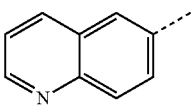

(connected via carbon 6). Such connections are in particular preferred in the composition of the present invention. However, in some cases connections via carbon 2, 3, 4, 5, and 7 are preferred. In other cases it is preferred that one or more than one quinoline moiety in a compound of Formula (Ia) is independently connected via carbon 6 or carbon 8, wherein one or more than one other quinoline moiety in the same compound is independently connected via one of the other carbon atoms in the quinoline moiety.

Furthermore (and preferably with respect to the above mentioned quinoline moieties), the respective ring structures among the $A^1$-, $A^2$-, and $A^3$-moieties are not connected by means of their nitrogen atoms (if available) with the rest of the compound of Formula (Ia) and Formula (Ib), respectively.

In the acidic aqueous composition for electrolytic copper plating according to the present invention (as defined above, preferably defined as being preferred) the $A^1$-, $A^2$-, and $A^3$-moieties are unsubstituted (also called not substituted). This means in particular that the hydrogen atoms in the ring structures are not covalently substituted. This preferably applies to quinoline moieties.

In the acidic aqueous composition for electrolytic copper plating according to the invention (as defined above, preferably defined as being preferred) $B^1$, $B^2$, $B^3$, $D^1$, $D^2$, and $D^3$ are independently selected from the group consisting of O and NH (including protonation states depending on the pH), preferably $B^1$, $B^2$, $B^3$, $D^1$, $D^2$, and $D^3$ are independently selected from the group consisting of O and NH with the proviso that $B^1$ is only NH if x is 1 and $A^1$ denotes

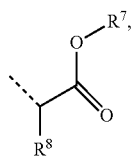

wherein $R^7$ and $R^8$ are independently selected from the group consisting of hydrogen, methyl, ethyl, linear C3 to C10 alkyl and branched C3 to C10 alkyl, (otherwise $B^1$ is O), $B^2$ is only NH if y is 1 and $A^2$ denotes

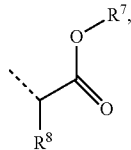

wherein $R^7$ and $R^8$ are independently selected from the group consisting of hydrogen, methyl, ethyl, linear C3 to C10 alkyl and branched C3 to C10 alkyl, (otherwise $B^2$ is O), $B^3$ is only NH if z is 1 and $A^3$ denotes

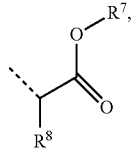

wherein $R^7$ and $R^8$ are independently selected from the group consisting of hydrogen, methyl, ethyl, linear C3 to C10 alkyl and branched C3 to C10 alkyl, (otherwise $B^3$ is O), more preferably $B^1$, $B^2$, $B^3$, $D^1$, $D^2$, and $D^3$ are independently selected from the group consisting of O and NH with the proviso that $B^1$ is only NH if x is 1 and $A^1$ denotes

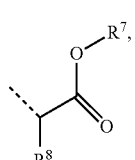

wherein $R^7$ and $R^8$ are independently selected from the group consisting of hydrogen, methyl, ethyl, linear C3 to C10 alkyl and branched C3 to C10 alkyl, (otherwise $B^1$ is O), $B^2$ is only NH if y is 1 and $A^2$ denotes

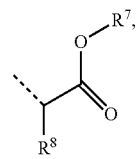

wherein $R^7$ and $R^8$ are independently selected from the group consisting of hydrogen, methyl, ethyl, linear C3 to C10 alkyl and branched C3 to C10 alkyl, (otherwise $B^2$ is O), $B^3$ is only NH if z is 1 and $A^3$ denotes

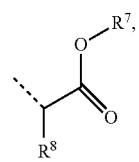

wherein $R^7$ and $R^8$ are independently selected from the group consisting of hydrogen, methyl, ethyl, linear C3 to C10 alkyl and branched C3 to C10 alkyl, (otherwise $B^3$ is O), $D^1$ is only NH if x is zero and o is 1, preferably if x is zero, o is 1, and $A^1$ denotes

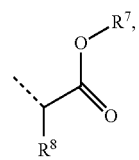

wherein $R^7$ and $R^8$ are independently selected from the group consisting of hydrogen, methyl, ethyl, linear C3 to C10 alkyl and branched C3 to C10 alkyl, (otherwise $D^1$ is O), $D^2$ is only NH if y is zero, preferably if y is zero and $A^2$ denotes

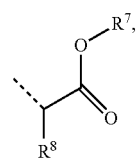

wherein $R^7$ and $R^8$ are independently selected from the group consisting of hydrogen, methyl, ethyl, linear C3 to C10 alkyl and branched C3 to C10 alkyl, (otherwise $D^2$ is O), and $D^3$ is only NH if z is zero, preferably if z is zero and $A^3$ denotes

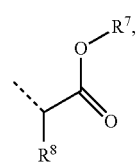

wherein $R^7$ and $R^8$ are independently selected from the group consisting of hydrogen, methyl, ethyl, linear C3 to C10 alkyl and branched C3 to C10 alkyl, (otherwise $D^3$ is O).

Preferably, $D^1$, $D^2$, and $D^3$, respectively, is NH if additionally to the above mentioned conditions for $D^1$, $D^2$, and $D^3$ a, b, and c is zero.

Preferably, $A^1$ (as defined above, preferably defined as being preferred) does not contain the moiety

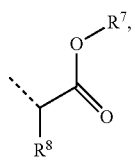

wherein $R^7$ and $R^8$ are independently selected from the group consisting of hydrogen, methyl, ethyl, linear C3 to C10 alkyl and branched C3 to C10 alkyl if $B^1$ and $D^1$ is O (correspondingly applying to $A^2$ in combination with $D^2$ and $B^2$ as well as to $A^3$ in combination with $D^3$ and $B^3$).

In the acidic aqueous composition according to the invention (as defined above, preferably defined as being preferred) $R^4$ and $R^5$ are independently selected from the group consisting of hydrogen, methyl, ethyl, linear C3 to C16 alkyl, branched C3 to C16 alkyl and a moiety of Formula (IIa) (as defined above). Preferably, $R^4$ and $R^5$ are independently selected from the group consisting of hydrogen, methyl, ethyl, linear C3 to C10 alkyl, branched C3 to C10 alkyl and a moiety of Formula (IIa) (as defined above). More preferably, $R^4$ and $R^5$ are independently selected from the group consisting of hydrogen, methyl, ethyl, linear C3 to C5 alkyl, branched C3 to C5 alkyl and a moiety of Formula (IIa) (as defined above). In some cases it is preferred that $R^4$ and $R^5$ are independently selected from the group consisting of hydrogen, methyl, ethyl, linear C3 to C5 alkyl and branched C3 to C5 alkyl. For specific moieties of linear C3 to C5 alkyl and branched C3 to C5 alkyl see the text above. In some cases it is preferred that $R^4$ is hydrogen if $R^5$ is a moiety of Formula (IIa) (as defined above).

In the acidic aqueous composition for electrolytic copper plating according to the invention (as defined above, preferably defined as being preferred) $A^1$, $A^2$ and $A^3$ independently comprise (besides other moieties for $A^1$, $A^2$ and $A^3$ as defined throughout the present text) linear C3 to C16 alkyl and branched C3 to C16 alkyl. Preferably, these alkyl moieties are linear C3 to C12 alkyl and branched C3 to C12 alkyl. For specific linear and branched C3 to C5 alkyl see the text above.

If $A^1$ is one of hydrogen, methyl, ethyl, linear C3 to C16 alkyl or branched C3 to C16 alkyl then the proviso preferably additionally includes that a is zero (applies correspondingly to $A^2$ in combination with b as well as to $A^3$ in combination with c).

In some cases it is preferred that $A^1$, $A^2$, and $A^3$ is not hydrogen. This means that preferably the group defined for $A^1$, $A^2$, and $A^3$ does not include hydrogen.

Preferably, in the acidic aqueous composition for electrolytic copper plating according to the invention (as defined above, preferably defined as being preferred) the total amount of component (ii) is at least 0.005 g/L, preferably at least 0.01 g/L, more preferably at least 0.1 g/L, and even more preferably at least 0.2 g/L, based on the total volume of the acidic aqueous composition. Preferably, the total amount is not exceeding 1 g/L, based on the total volume of the acidic aqueous composition, preferably not exceeding 100 mg/L, more preferably not exceeding 10 mg/L.

In the acidic aqueous composition for electrolytic copper plating according to the present invention (as defined above, preferably defined as being preferred) the sum of o, p, q, and t (o+p+q+t) is in the range of from 5 to 300 (o+p+q+t=5 to 300). Each individually, o, p, q, and t are in the range of from 0 to 300, preferably in the range of from 0 to 100, more preferably in the range of from 0 to 50 (with the proviso defined for the aforementioned sum). This means o, p, q, and t are positive integers including the value zero. They contribute to said sum if the respective moiety is present in the compound of Formula (Ia) and (Ib), respectively, otherwise they contribute with zero.

In the acidic aqueous composition for electrolytic copper plating according to the present invention (as defined above, preferably defined as being preferred) is preferred, wherein o+p+q+t=6 to 100, preferably o+p+q+t=7 to 50, more preferably o+p+q+t=8 to 30. In some cases it is preferred that o is 1 if $D^1$ is NH.

In the acidic aqueous composition for electrolytic copper plating according to the present invention (as defined above, preferably defined as being preferred) is preferred, wherein at least one of a, b, and c (preferably a) is zero, more preferably at least two of a, b, and c (preferably a and b) are zero, even more preferably a, b, and c are zero.

Preferably, a is zero if $A^1$ is a moiety selected from the group consisting of

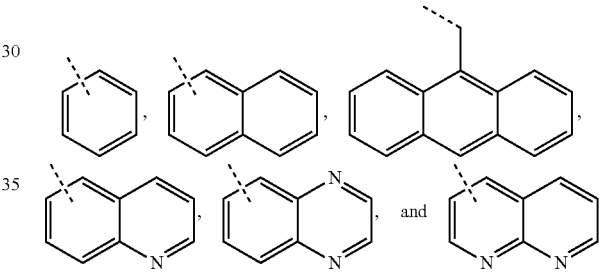

(preferably, a is zero if $A^1$ is defined as being preferred throughout the present text). This correspondingly applies to b and $A^2$ as well as to c and $A^3$.

In some cases an acidic aqueous composition of the present invention is preferred, wherein a, b, and c are independently 0 (zero) or 1.

In some cases the following component (ii) is preferred in an acidic aqueous composition according to the present invention:

(ii) one or more than one compound of Formula (Ia)

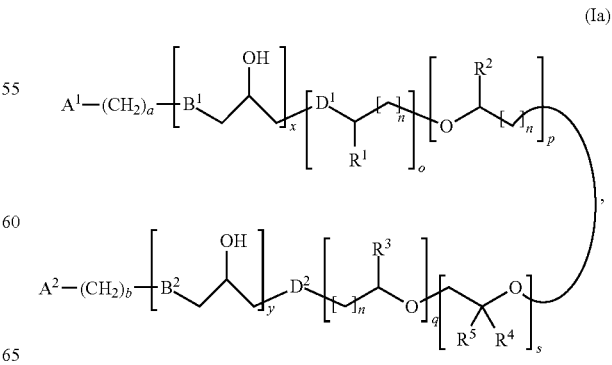

wherein
R$^4$ and R$^5$ are independently selected from the group consisting of hydrogen, methyl, ethyl, linear C3 to C16 alkyl, branched C3 to C16 alkyl and a moiety of Formula (IIa)

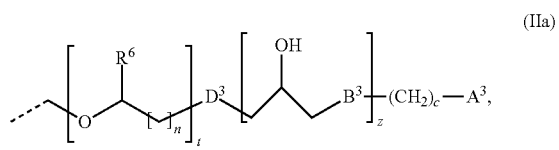
(IIa)

R$^1$, R$^2$, R$^3$ and R$^6$ are independently selected from the group consisting of hydrogen, methyl and ethyl, B$^1$ and D$^1$ are O (oxygen), B$^2$, B$^3$, D$^2$, and D$^3$ are independently selected from the group consisting of O and NH, A$^1$, A$^2$ and A$^3$ independently denote a moiety selected from the group consisting of
  hydrogen, methyl, ethyl, linear C3 to C16 alkyl and branched C3 to C16 alkyl,

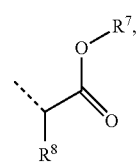

wherein R$^7$ and R$^8$ are independently selected from the group consisting of hydrogen, methyl, ethyl, linear C3 to C10 alkyl and branched C3 to C10 alkyl, and

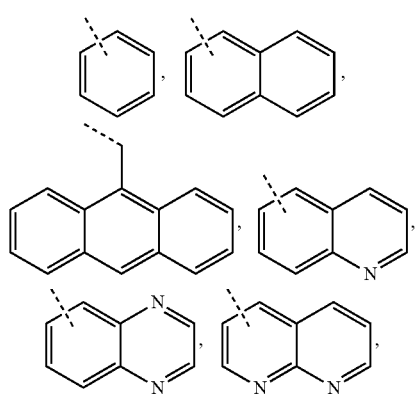

with the proviso that
  at least A$^1$ (out of A$^1$, A$^2$, and A$^3$) is a moiety selected from the group consisting of

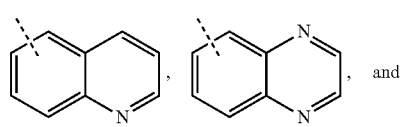
and

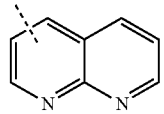

(preferably A$^1$ is a moiety defined as being preferred throughout the present text), a, b and c are independently 0, 1, 2 or 3 (preferably a is zero and b and c are independently 0, 1, 2 or 3), S, x, y, and z are independently 0 or 1, n independently is 1, 2 or 3, o+p+q+t=5 to 300.

The aforementioned preferred features of an acidic aqueous composition for electrolytic copper plating according to the present invention (comprising a compound of Formula (Ia)) do also apply (if technically and/or scientifically applicable) for an acidic aqueous composition for electrolytic copper plating comprising a compound of Formula (Ib) (for further details see the text below) and for other preferred features described in the text below.

In some cases an acidic aqueous composition for electrolytic copper plating according to the present invention (as defined above, preferably defined as being preferred) is preferred, wherein B$^1$, B$^2$, B$^3$, D$^1$, D$^2$, and D$^3$ denote O (an oxygen atom). Thus, an acidic aqueous composition for electrolytic copper plating, (preferably) according to the present invention (as defined above, preferably defined as being preferred) is preferred, comprising
  (i) copper (II) ions,
  (ii) one or more than one compound of Formula (Ib)

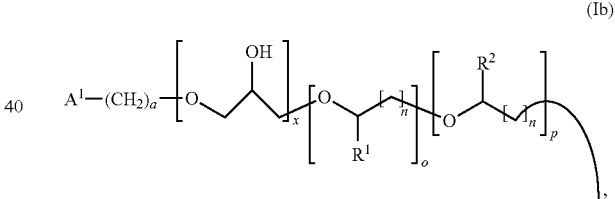
(Ib)

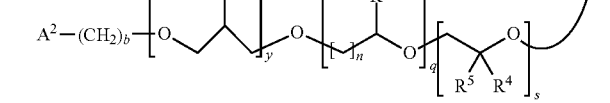

wherein
R$^4$ and R$^5$ are independently selected from the group consisting of hydrogen, methyl, ethyl, linear C3 to C16 alkyl, branched C3 to C16 alkyl and a moiety of Formula (IIb)

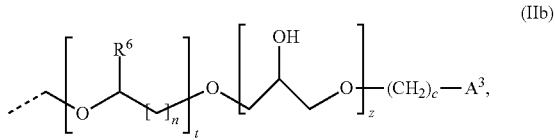
(IIb)

R$^1$, R$^2$, R$^3$ and R$^6$ are independently selected from the group consisting of hydrogen, methyl and ethyl, A¹, A² and A³ independently denote a moiety selected from the group consisting of hydrogen, methyl, ethyl, linear C3 to C16 alkyl and branched C3 to C16 alkyl,

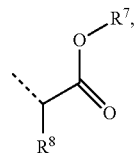

wherein $R^7$ and $R^8$ are independently selected from the group consisting of hydrogen, methyl, ethyl, linear C3 to C10 alkyl and branched C3 to C10 alkyl, and

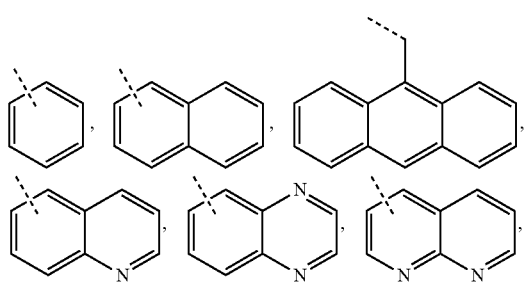

with the proviso that at least one of A¹, A² and A³ is a moiety selected from the group consisting of

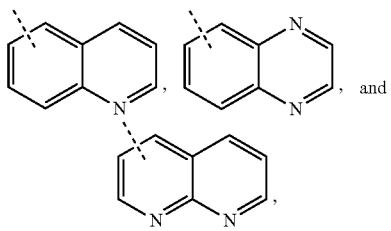

a, b and c are independently 0, 1, 2 or 3, s, x, y, and z are independently 0 or 1, n independently is 1, 2 or 3, o+p+q+t=5 to 300, and (iii) one, two, three or more than three further compounds, which are different from the compound of Formula (Ib).

The above stated regarding the pH of the composition applies likewise.

Our own experiments have shown that a respective composition (wherein B¹, B², B³, D¹, D², and D³ denote O (an oxygen atom)) in many cases exhibits a very good stability (shelf life).

In some cases it is preferred that, if B¹, B², B³, D¹, D², and D³ is O (oxygen), the moiety A¹, A² and A³ (as defined above) does not contain

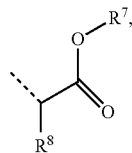

wherein $R^7$ and $R^8$ are defined as above.

An acidic aqueous composition for electrolytic copper plating according to the present invention (as defined above, preferably defined as being preferred) is preferred, wherein A¹, A² and A³ independently denote a moiety selected from the group consisting of hydrogen, methyl, ethyl, linear C3 to C16 alkyl and branched C3 to C16 alkyl,

wherein $R^7$ and $R^8$ are independently selected from the group consisting of hydrogen, methyl, ethyl, linear C3 to C10 alkyl and branched C3 to C10 alkyl, and

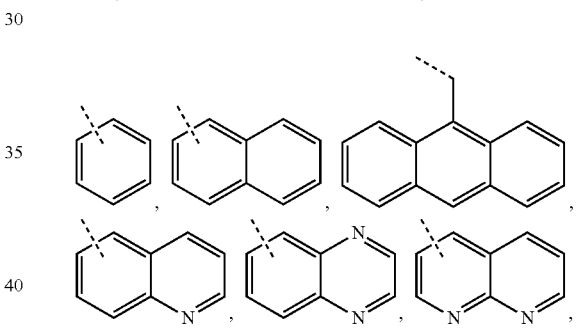

with the proviso that at least one of A¹, A² and A³ is

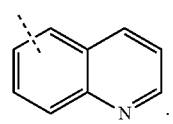

Thus, most preferred is that at least one of A¹, A² and A³ is (unsubstituted) quinoline. This means that a composition of the present invention is preferred, wherein at least one of A¹, A² and A³ is

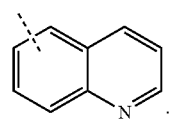

The aforementioned provisos (including the preferred embodiments) apply to the compound of Formula (Ia) and (Ib), respectively. In case of Formula (Ia) it applies with the additional proviso that the corresponding $B^1$, $B^2$, and $B^3$ of the at least one of $A^1$, $A^2$ and $A^3$ is O if the corresponding x, y, and z is 1.

The term "the corresponding $B^1$, $B^2$, and $B^3$ of the at least one of $A^1$, $A^2$ and $A^3$ is O if the corresponding x, y, and z is 1" defines that if e.g. $A^1$ is selected for the proviso (e.g. being a quinoline), $B^1$ is corresponding to $A^1$ and x is corresponding to $B^1$ (the same applies to $A^2$ in combination with $B^2$ and y, and $A^3$ in combination with $B^3$ and z).

An acidic aqueous composition for electrolytic copper plating according to the present invention (as defined above, preferably defined as being preferred) is preferred, wherein $A^1$, $A^2$ and $A^3$ independently denote a moiety selected from the group consisting of hydrogen, methyl, ethyl, linear C3 to C16 alkyl, and branched C3 to C16 alkyl,

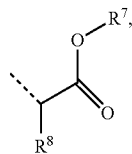

wherein $R^7$ and $R^8$ are independently selected from the group consisting of hydrogen, methyl, ethyl, linear C3 to C10 alkyl and branched C3 to C10 alkyl, and

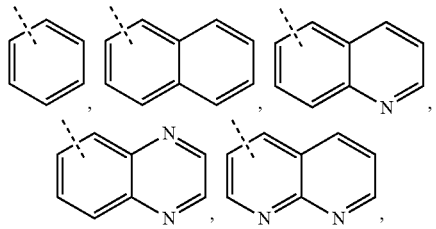

with the proviso that
at least one of $A^1$, $A^2$ and $A^3$ is a moiety selected from the group consisting of

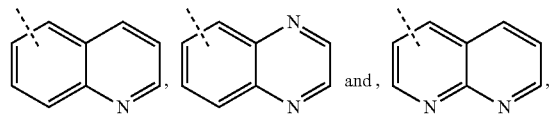

preferably at least one of $A^1$, $A^2$ and $A^3$ is

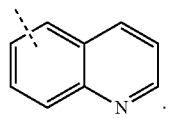

The aforementioned proviso (including the preferred embodiments) applies to the compound of Formula (Ia) and (Ib), respectively. In case of Formula (Ia) it applies with the additional proviso that the corresponding $B^1$, $B^2$, and $B^3$ of the at least one of $A^1$, $A^2$ and $A^3$ is O if the corresponding x, y, and z is 1.

In other words, a composition of the present invention is preferred, wherein $A^1$, $A^2$, and $A^3$ independently denote a moiety selected from the group consisting of hydrogen, methyl, ethyl, linear C3 to C16 alkyl, and branched C3 to C16 alkyl,

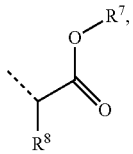

wherein $R^7$ and $R^8$ are independently selected from the group consisting of hydrogen, methyl, ethyl, linear C3 to C10 alkyl and branched C3 to C10 alkyl, and

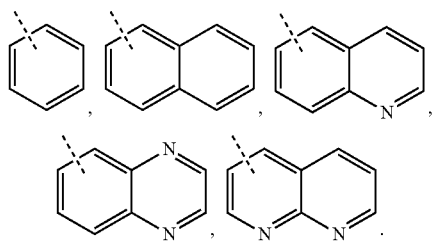

An acidic aqueous composition for electrolytic copper plating according to the present invention (as defined above, preferably defined as being preferred) is preferred, wherein $A^1$, $A^2$ and $A^3$ independently denote a moiety selected from the group consisting of hydrogen, methyl, ethyl, linear C3 to C14 alkyl, and branched C3 to C14 alkyl,

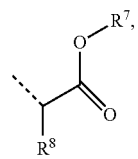

wherein $R^7$ and $R^8$ are independently selected from the group consisting of hydrogen, methyl, ethyl, linear C3 to C10 alkyl and branched C3 to C10 alkyl, and

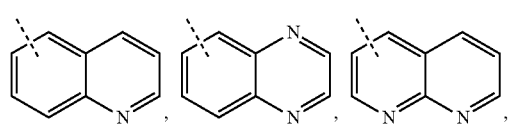

with the proviso that
at least one of $A^1$, $A^2$ and $A^3$ is a moiety selected from the group consisting of

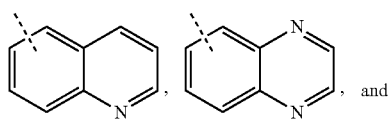

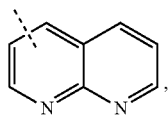

preferably at least one of $A^1$, $A^2$ and $A^3$ is

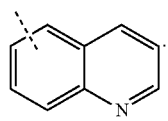

The aforementioned proviso (including the preferred embodiments) applies to the compound of Formula (Ia) and (Ib), respectively. In case of Formula (Ia) it applies with the additional proviso that the corresponding $B^1$, $B^2$, and $B^3$ of the at least one of $A^1$, $A^2$ and $A^3$ is O if the corresponding x, y, and z is 1.

In other words, a composition of the present invention is preferred, wherein $A^1$, $A^2$, and $A^3$ independently denote a moiety selected from the group consisting of hydrogen, methyl, ethyl, linear C3 to C14 alkyl, and branched C3 to C14 alkyl,

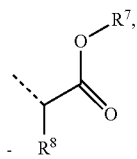

wherein $R^7$ and $R^8$ are independently selected from the group consisting of hydrogen, methyl, ethyl, linear C3 to C10 alkyl and branched C3 to C10 alkyl, and

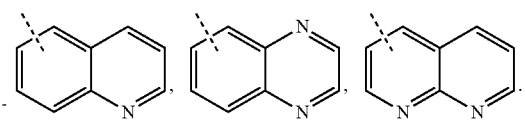

In some cases an acidic aqueous composition for copper plating according to the invention (as defined above, preferably defined as being preferred) is preferred, wherein at least two of $A^1$, $A^2$ and $A^3$ is a moiety selected from the group consisting of

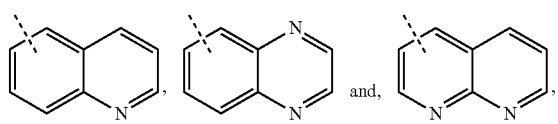

preferably at least two of $A^1$, $A^2$ and $A^3$ is

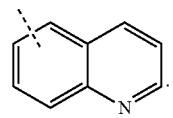

As mentioned above in the text, $A^1$, $A^2$, and $A^3$ moieties containing a ring structure (e.g. quinoline) are unsubstituted, preferably (all) $A^1$, $A^2$, and $A^3$ moieties are unsubstituted. The latter means that for example no additional hetero atoms are present, such as halogen atoms or other functional groups (e.g. hydroxyl, nitro, amino etc.).

An acidic aqueous composition for electrolytic copper plating according to the invention (as defined above, preferably defined as being preferred) is preferred, wherein $R^7$ and $R^8$ are independently selected from the group consisting of hydrogen, methyl, ethyl, n-propyl, iso-propyl, n-butyl, iso-butyl, sec-butyl, tert-butyl,

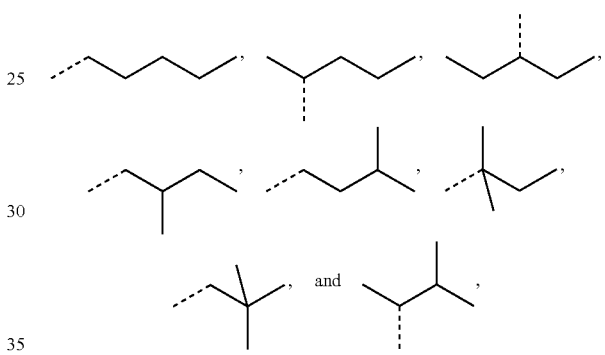

wherein the dashed line represents the covalent bond for binding the respective carbon atom of the radical with the respective atom of

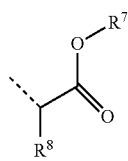

(connecting bond). Most preferably, $R^7$ is selected from the group consisting of hydrogen and iso-propyl and $R^8$ is iso-butyl.

In some cases an acidic aqueous composition for electrolytic copper plating according to the present invention (as defined above, preferably defined as being preferred) is preferred, wherein at least one of x, y, and z is 0 (zero), preferably x, y, and z are 0 (zero). In such a case the number of hydroxyl groups in the compound of Formula (Ia) and (Ib), respectively, is reduced, preferably the compound does not contain any hydroxyl group. According to our own experiments such compounds typically exhibit strong adhesion strength to the surface of a substrate and to copper surfaces. However, in some cases an acidic aqueous composition for electrolytic copper plating according to the present invention (as defined above, preferably defined as being preferred) is preferred, wherein at least one of x, y, and z is 1, preferably x, y, and z are 1. In such a case the number of hydroxyl groups in the compound of Formula (Ia) and (Ib), respectively, is comparatively high. According to our own experiments such compounds typically exhibit lower adhesion strength to the surface of a substrate and to copper surfaces. However, lower adhesion strength in many cases leads to a decreased co-deposition of said compounds in the deposited copper. Nevertheless, irrespective of x, y, and z being zero or one, the overpotential generated in respective compositions is considerably high compared to the overpotential generated in a composition comprising PEG (see "Examples" below).

As mentioned above, the acidic aqueous composition for electrolytic copper plating according to the present invention (as defined above, preferably defined as being preferred) comprises one, two, three or more than three further compounds, which are different from the compound of Formula (Ia) and the compound of Formula (Ib), respectively. Preferably, the one, two, three or more than three further compounds are selected from the group consisting of one or more than one species of inorganic ions, one or more than one accelerator-brightener compound, one or more than one carrier-suppressor compound, one or more than one leveler compound, and one or more than one wetting agent.

Preferably, the composition of the present invention is substantially free of, preferably does not comprise, complexing agents.

A preferred species of inorganic ions is selected from the group consisting of halide ions (preferably chloride ions) and sulphate ions. They may be fully or partly added to the acidic aqueous composition according to the present invention by means of the copper source (for various copper sources see the text above). Other suitable sources for halide ions are for example hydrochloric acid or alkali halides such as sodium chloride.

Preferred is a composition of the present invention, wherein the one, two, three or more than three further compounds comprise halide ions, preferably chloride ions.

Preferably, in the acidic aqueous composition for electrolytic copper plating according to the present invention (as defined above, preferably defined as being preferred) the total amount of chloride ions is in the range of from 0.01 to 0.18 g/L, preferably in the range of from 0.03 to 0.10 g/L, based on the total volume of the acidic aqueous composition. Preferably, the total amount of hydrochloric acid is in the range of from 0.01 to 0.18 g/L, preferably in the range of from 0.03 to 0.10 g/L, based on the total volume of the acidic aqueous composition The acidic aqueous composition for electrolytic copper plating according to the present invention (as defined above, preferably defined as being preferred) preferably contains sulfuric acid. Preferably, the total amount of sulfuric acid added in order to prepare a composition according to the present invention is in the range of from 5 g/L to 350 g/L, preferably in the range of from 8 g/L to 220 g/L, based on the total volume of the acidic aqueous composition. More preferred is a total amount in the range of from 8 g/L to 90 g/L or 180 g/L to 220 g/L. The sulfuric acid can also be replaced partially or completely by fluoroboric acid, methane sulfonic acid or other acids.

In some cases it is preferred that the acidic aqueous composition according to the present invention comprises a redox couple, more preferably Fe (II)/Fe (III) ions. Such a redox couple is particularly useful, if reverse pulse plating is used in combination with inert anodes for copper deposition. Suitable processes for copper plating using a redox couple in combination with reverse pulse plating and inert anodes are for example disclosed in U.S. Pat. Nos. 5,976,341 and 6,099,711.

Preferred accelerator-brightener compounds are selected from the group consisting of thiol-, sulphide-, disulphide- and polysulphide-compounds. More preferred accelerator-brightener compounds are selected from the group consisting of 3-(benzthiazolyl-2-thio)-propyl sulphonic-acid, 3-mercaptopropan-1-sulphonic acid, ethylendithiodipropyl sulphonic-acid, bis-(p-sulphophenyl)-disulphide, bis-(ω-sulphobutyl)-disulphide, bis-(ω-sulphohydroxypropyl)-disulphide, bis-(ω-sulphopropyl)-disulphide, bis-(ω-sulphopropyl)-sulphide, methyl-(ω-sulphopropyl)-disulphide, methyl-(ω-sulfopropyl)-trisulphide, O-ethyl-dithiocarbonic-acid-S-(ω-sulphopropyl)-ester, thioglycolic acid, thiophosphoric-acid-O-ethyl-bis-(ω-sulphopropyl)-ester, 3-N, N-dimethylaminodithiocarbamoyl-1-propanesulphonic acid, 3,3'-thiobis(1-propanesulphonic acid), thiophosphoric-acid-tris-(ω-sulphopropyl)-ester and their corresponding salts. The total amount of accelerator-brightener compounds is preferably in the range of from 0.01 mg/L to 100 mg/L, more preferably in the range of from 0.05 mg/L to 10 mg/L, based on the total volume of the acidic aqueous composition.

Preferred carrier-suppressor compounds are selected from the group consisting of polyvinyl alcohol, carboxymethylcellulose, polyethylene glycol, polypropylene glycol, stearic acid polyglycolester, alkoxylated naphtols, oleic acid polyglycolester, stearylalcoholpolyglycolether, nonylphenolpolyglycolether, octanolpolyalkylenglycolether, octanediol-bis-(polyalkylenglycolether), poly(ethylenglycol-ran-propylenglycol), poly(ethylenglycol)-block-poly(propyleneglycol)-block-poly(ethylenglycol), and poly(propylenglycol)-block-poly(ethylenglycol)-block-poly(propylenglycol). More preferably, the carrier-suppressor compound is selected from the group consisting of polyethylene glycol, polypropylene glycol, poly(ethylene glycol-ran-propylene glycol), poly(ethylenglycol)-block-poly(propyleneglycol)-block-poly(ethylenglycol), and poly(propylenglycol)-block-poly(ethylenglycol)-block-poly(propylenglycol). The total amount of carrier-suppressor compounds is preferably in the range of from 0.005 g/L to 20 g/L, more preferably in the range of from 0.01 g/L to 5 g/L.

Own reference experiments have shown that acidic aqueous reference compositions (not according to the present invention; i.e. without a compound of Formulae (Ia) and (Ib), respectively) comprising carrier-suppressor compounds (e.g. as defined above) very often result in a smoother, more homogeneous copper surfaces, compared to a copper surface obtained in the absence of such a carrier-suppressor compound. Furthermore, many of the aforementioned compounds typically contribute to an adequate overpotential in the respective reference compositions. However, the overpotential obtained in such a reference composition is usually considerably lower compared to an acidic aqueous composition according to the present invention. Thus, in some cases it is preferred that the acidic aqueous composition according to the present invention is substantially free of, preferably does not contain one or more than one carrier-suppressor compound selected from the group consisting of polyvinyl alcohol, carboxymethylcellulose, polyethylene glycol, polypropylene glycol, stearic acid polyglycolester, alkoxylated naphtols, oleic acid polyglycolester, stearylalcoholpolyglycolether, nonylphenolpolyglycolether, octanolpolyalkylenglycolether, octanediol-bis-(polyalkylenglycolether), poly(ethylenglycol-ran-propylenglycol), poly(ethylenglycol)-block-poly(propyleneglycol)-block-poly(ethylenglycol), and poly(propylenglycol)-block-poly(ethylenglycol)-block-poly(propylenglycol). However, in other cases it appears acceptable to additionally include one or more than one carrier-suppressor compound as defined above. In many cases, our own experiments have shown that the comparatively high overpotential generated in the acidic aqueous compositions according to the present invention is not negatively affected in the presence of additional carrier-suppressor compounds as defined above.

Preferred leveler compounds are selected from the group consisting of nitrogen containing leveler compounds such as polyethyleneimine, alkoxylated polyethyleneimine, alkoxylated lactams and polymers thereof, diethylenetriamine and hexamethylenetetramine, dyes such as Janus Green B, Bismarck Brown Y and Acid Violet 7, sulphur containing amino acids such as cysteine, and phenazinium salts. Further nitrogen containing levelers can be polyethylenimine bearing peptides, polyethylenimine bearing amino acids, polyvinylalcohol bearing peptides, polyvinylalcohol bearing amino acids, polyalkyleneglycol bearing peptides, polyalkyleneglycol bearing amino acids, aminoalkylen bearing pyrroles and aminoalkylen bearing pyridines. Suitable ureyl polymers have been disclosed in EP 2735627 A$^1$, said polyalkyleneglycol bearing amino acids and peptides are published in EP 2113587 B9. EP 2537962 A$^1$ teaches suitable aminoalkylene compounds bearing pyrroles and pyridines. The total amount of leveler compounds in the acidic aqueous composition according to the present invention is preferably in the range of from 0.1 mg/L to 100 mg/L, based on the total volume of the composition. Own experiments have shown that such leveler compounds very often improve the process stability.

In a few cases, according to our own experiments, some leveler compounds as defined above slightly negatively (but still acceptably) affect the overpotential generated in the acidic aqueous compositions according to the invention. Thus, in a few cases it is preferred that the acidic aqueous composition according to the present invention (as defined above, preferably defined as being preferred) is substantially free of, preferably does not contain one or more than one leveler compound as defined above.

Preferably, the acidic aqueous composition according to the present invention contains at least one wetting agent. These wetting agents are also referred to as surfactants in the art. The at least one wetting agent is preferably selected from the group consisting of non-ionic, cationic and anionic surfactants. The total amount of wetting agents in the acidic aqueous composition according to the present invention is preferably in the range of from 0.01 to 5 wt.-%, based on the total weight of the acidic aqueous composition.

As mentioned above, the acidic aqueous composition according to the invention contains one or more than one compound of Formula (Ia) and (Ib), respectively. Preferably, in the acidic aqueous composition according to the present invention the weight average molecular weight (Mw) of the total amount of the one or more than one compounds of Formula (Ia) (and Formula (Ib) respectively) is in the range of from 300 g/mol to 10000 g/mol, preferably in the range of from 400 g/mol to 8000 g/mol preferably in the range of from 500 g/mol to 4000 g/mol.

According to our own experiments, excellent results were obtained, if the acidic aqueous composition according to the present invention preferably comprises one, more than one or all compounds selected from the group consisting of

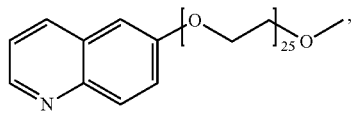
(a)

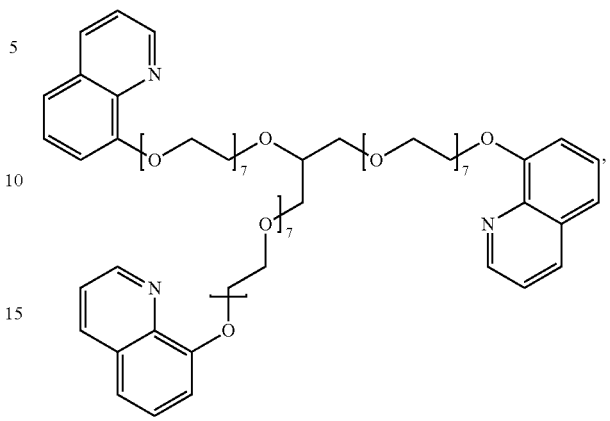
(b)

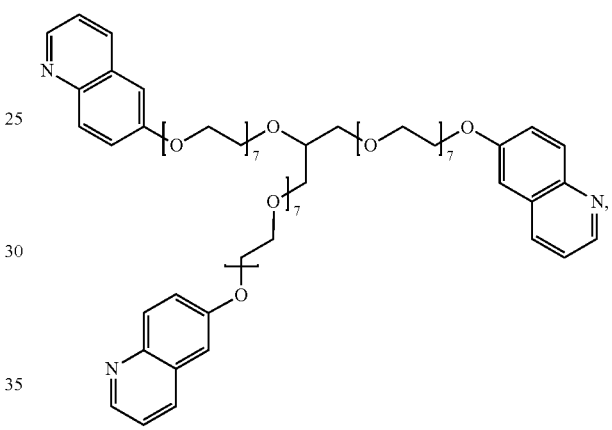
(c)

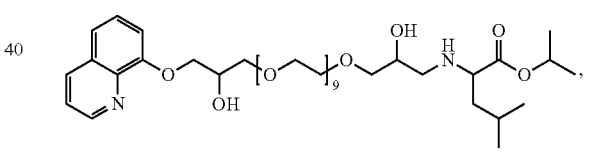
(d)

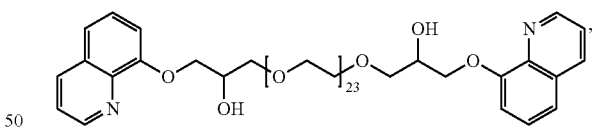
(e)

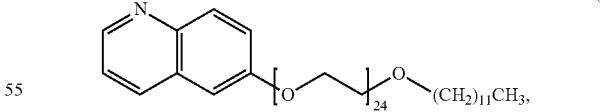
(f)

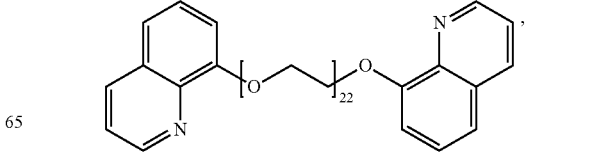
(g)

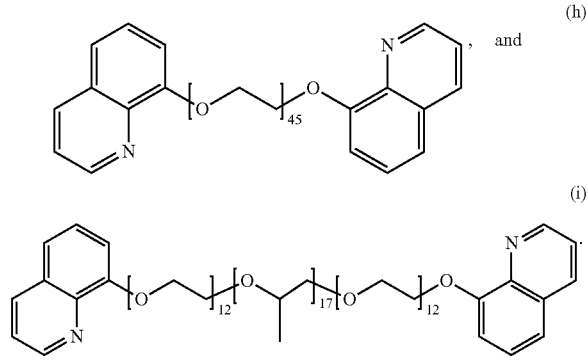

Thus, a respective acidic aqueous composition for electrolytic copper plating according to the present invention (as defined above, preferably defined as being preferred) is in particular preferred. These are very preferred specific compounds of Formula (Ia) (respectively of Formula (Ib)) and, thus, result in very preferred compositions of the present invention comprising a compound of generic Formula (Ia) (respectively of Formula (Ib)).

The present invention also relates to the use of the acidic aqueous composition according to the present invention (as defined above, preferably defined as being preferred) for electrolytic copper plating, preferably for void-free copper filling of recessed structures (preferably recessed structures with an aspect ratio in the range from 1:1 to 20:1). Preferred recessed structures are trenches, blind micro vias, and through holes.

The above mentioned features regarding the acidic aqueous composition according to the present invention (preferably features defined as being preferred) do also apply to the use of the acidic aqueous composition for electrolytic copper plating and void-free copper filling.

The present invention relates also to the use of the compound of Formula (Ia) as defined in the text above and of the compound of Formula (Ib) as defined in the text above, respectively, in an acidic aqueous composition for electrolytic metal plating, preferably in an acidic aqueous composition for electrolytic copper plating, preferably in an acidic aqueous composition for electrolytic copper plating according to the present invention (as defined above, preferably defined as being preferred). Preferably said compounds are used in the composition in order to increase the overpotential, i.e. as an overpotential increasing compound.

The term "as an over potential increasing compound" means that the compound of Formula (Ia) as defined in the text above and the compound of Formula (Ib) as defined in the text above, respectively, increases the overpotential compared to a comparative experiment, which is carried out identically but with the only difference that polyethylene glycol is used as an overpotential increasing compound instead of a compound of Formula (Ia) as defined in the text above or a compound of Formula (Ib) as defined in the text above, respectively. An overpotential is increased (in the context of the present invention) if the potential is higher compared to the potential obtained with polyethylene glycol (preferably with PEG 3000) as a replacement of component (ii); the respective experiments otherwise being identical. A skilled person can easily determine the overpotential by a series of standard injection experiments (see "Examples").

The above mentioned features regarding the acidic aqueous composition (as defined above, preferably defined as being preferred), do also apply to the aforementioned use of the acidic aqueous composition for electrolytic copper plating and to the aforementioned use of the compound.

The present invention relates furthermore to a method of electrolytic copper plating, comprising the steps
(a) providing or manufacturing a substrate suitable for electrolytic copper plating,
(b) contacting the substrate obtained in step (a), or obtained in an additional step after step (a) but before step (b), with the acidic aqueous composition according to the present invention (as defined above, preferably defined as being preferred) and applying an electrical current such that copper is electrolytically plated onto the substrate.

In the method according to the present invention the substrate and at least one anode are connected to a current or respective voltage source. Upon applying a current, copper is plated (deposited) onto said substrate (at least on parts of the substrate's surface). In some cases step (b) is carried out directly after step (a). In other cases it is preferred that after step (a) a cleaning and/or rinsing step is included as an additional step. In such a case a cleansed/rinsed substrate is obtained. Preferably, such a cleansed/rinsed substrate is directly contacted as defined in step (b).

Preferably, the substrate is selected from the group consisting of printed circuit boards, IC substrates, semiconducting wafers, ceramics and glass substrates. Preferred are substrates of the aforementioned group which have recessed structures such as trenches, blind micro vias, through silicon vias, through holes and through glass vias. Therefore, a substrate is preferred comprising one or more than one recessed structure selected from the group consisting of trenches, blind micro vias, and through holes. In the method of the present invention preferably these structures are void-free filled with copper (see "Examples" below). Thus, preferred is a method of the present invention, wherein in step (b) an electrical current is applied such that copper is electrolytically plated onto the substrate and recessed structures, preferably trenches, blind micro vias, and through holes are void-free filled with copper.

In many cases it is preferred that the substrate contains a metal seed layer, more preferably a copper seed layer. In some cases, the substrate preferably comprises a resin, ceramics, glass, or silicon, more preferably with a metal seed layer, even more preferably with a copper seed layer.

During the method of electrolytic copper plating according to the present invention, the acidic aqueous composition according to the present invention is preferably agitated, more preferably by a strong inflow and, where applicable, by clean air being blown in, such that the surface of the composition undergoes strong movement. This means that the substance transport is maximized in the vicinity of the cathodes and anodes so that a greater current density is made possible.

Movement of the cathodes also improves the substance transport at the respective surfaces. In addition, convection can also be produced in the composition by rotating the substrate. Constant diffusion-controlled deposition is achieved by means of the increased convection and electrode movement. The substrate can be moved in a horizontal and vertical manner and/or by means of vibration. A combination with the air blown into the composition is particularly effective, and, thus preferred.

In the method of electrolytic copper plating according to the present invention (as described above, preferably described as being preferred) step (b) is preferably carried out at a temperature in the range of from 15° C. to 50° C., more preferably at a temperature in the range of from 15° C. to 40° C. This means that in step (b) the composition of the present invention has a temperature as defined above.

Preferably, a cathodic current density (average density) in the range of from 0.05 A/dm$^2$ to 12 A/dm$^2$ is applied, more preferably in the range of from 0.1 A/dm$^2$ to 7 A/dm$^2$, even more preferably in the range of from 0.1 A/dm$^2$ to 3 A/dm$^2$. However, current densities exceeding the above mentioned ranges are not excluded, in particular for pulse plating methods.

Preferably, step (b) in the method of electrolytic copper plating according to the present invention (as described above, preferably described as being preferred) is carried out in DC plating mode (DC plating method), pulse plating mode including reverse pulse plating mode (pulse plating method and reverse pulse plating method, respectively) or in combinations thereof.

Pulse plating typically includes unipolar pulsed currents, wherein the depositing current is regularly interrupted by current pauses. Reverse pulse plating typically includes pulses of reversed currents during the plating process.

The reverse pulse plating method was developed for the electrolytic deposition in particular of copper on circuit boards with a high aspect ratio and is described, for example, in DE 42 25 961 C2 and DE 27 39 427 A 1. Where higher current densities are used, improved surface distribution and throwing power is achieved in the through holes.

In the method of the present invention (as defined above, preferably defined as being preferred), inert (insoluble) or soluble anodes are used. In some cases inert anodes are preferred. Insoluble anodes are inert during the plating process and consequently do not change their shape. This enables a time constant geometry during the plating process. In particular precious metals, such as platinum or also so-called valve metals such as titanium, coated with mixed oxides of precious metals, for example with a coating of ruthenium oxide and iridium oxide, are preferably used as insoluble anodes in the method according to the present invention. In some cases it is preferred that the insoluble anodes are in the form of expanded metal. In order to obtain a supplement of copper ions when using insoluble anodes, a copper compound needs to be dissolved in the acidic aqueous composition according to the present invention (for copper sources see the text above), or metallic copper is brought into contact with the composition. Metallic copper dissolves under the influence of oxygen dissolved in the composition or with the help of compounds that form the oxidised form of a redox system, for example with the help of Fe (III) ions dissolved in the composition which are thereby reduced to Fe (II) ions. The Fe (II) ions are oxidised at the insoluble anode back to Fe (III) ions. The Fe (II)/Fe (III) ions can originate, for example, from a corresponding iron sulfate salt. The concentration of Fe (II) ions in the composition is preferably 8 to 12 g/L and that of Fe (III) ions preferably 1 to 5 g/L, based on the total volume of the composition.

However, in other cases soluble copper anodes are preferred. The copper consumed during the deposition (plating) process is typically supplemented electrochemically via soluble copper anodes. Soluble copper anodes with a content of 0.02 to 0.067 percent by weight phosphorus are in particular preferred.

In the method according to the present invention, copper is preferably plated both in the conventional manner, by immersing the substrate into the composition that is located in an immersion bath container and polarizing the substrate in relation to an anode that is located in the same composition, and also by a horizontal plating method. The latter plating method is carried out in a conventional horizontal apparatus, through which the substrates are conveyed in a horizontal position and direction of transport, at the same time being brought into contact with the acidic aqueous composition. The anodes are also disposed in a horizontal position in the apparatus along the transport path for the substrates. These types of apparatus are disclosed, for example, in DE 36 24 481 A1 and DE 32 36 545 A1. In addition, semiconductor wafers are preferably treated in so-called cup-platers, in which a respective wafer is disposed in the horizontal position above an anode that is also disposed in a horizontal position. The cup-plater is filled with the acidic aqueous composition according to the present invention. Consequently, both the wafer and the anode are in contact with the composition. Preferably, the wafer rotates during the depositing process.

Furthermore, the above mentioned features regarding the acidic aqueous composition (as defined above, preferably defined as being preferred), preferably do also apply to the method of electrolytic copper plating according to the present invention.

Furthermore, the present invention relates to a compound of Formula (Ia) and Formula (Ib), respectively, wherein the compound is selected from the group consisting of

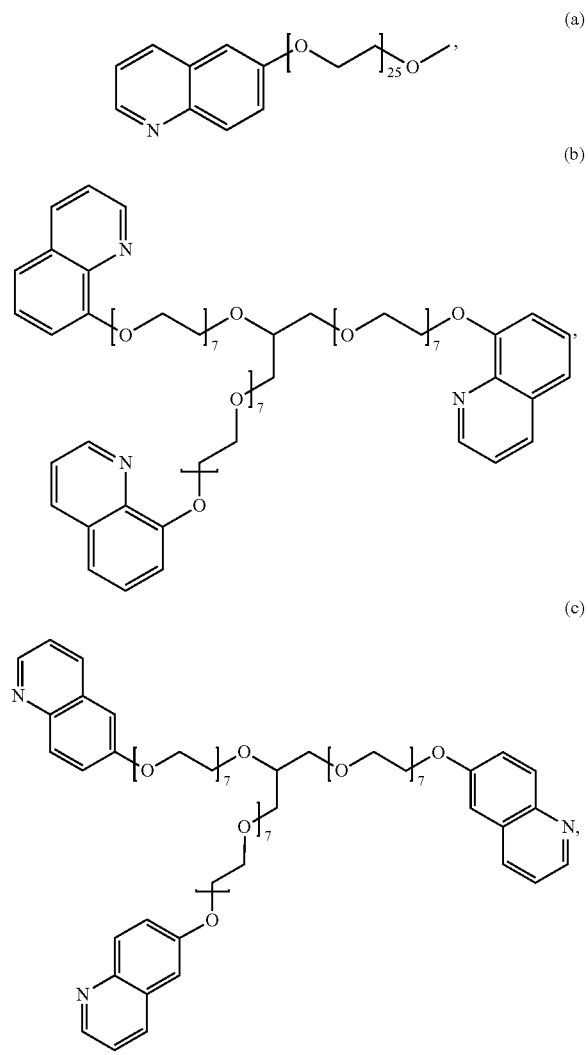

-continued

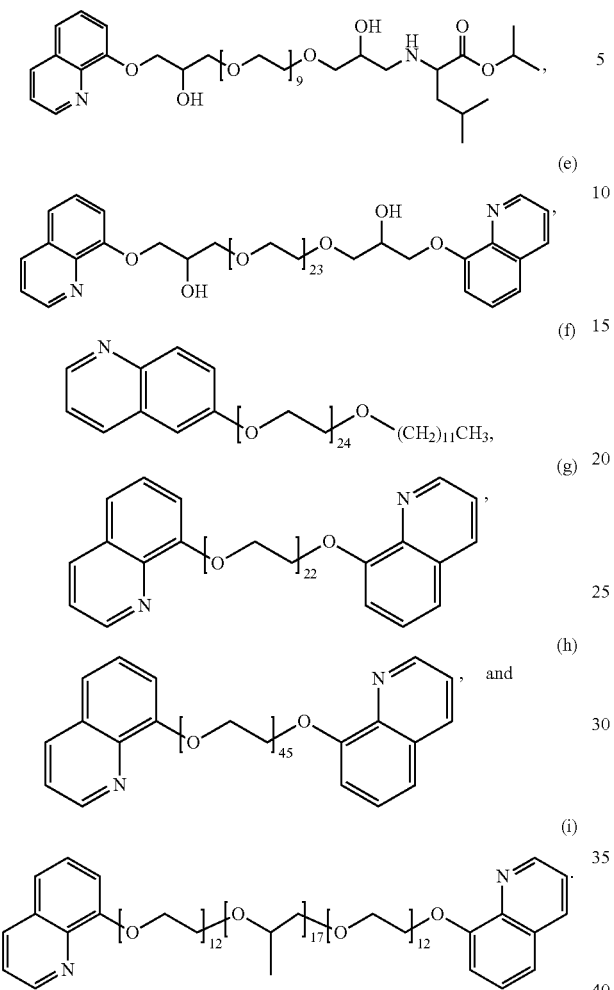

According to our own experiments, these compounds showed very good plating results and sufficiently high overpotentials compared to PEG (see section "Examples" below). They are for an acidic aqueous composition for electrolytic metal plating, preferably for electrolytic copper plating, more preferably for a composition and method, respectively, as defined for the present invention.

The following examples illustrate the benefits of the acidic aqueous composition according to the present invention and the benefits of the method of electrolytic copper plating according to the present invention.

EXAMPLES

A. Experiments and Results (Copper Filling)

1. Example 1 (According to the Invention, Compound of Formula (a))

1.1 Synthesis

In a first step 1.41 g 6-hydroxyquinoline (9 mmol) was dissolved in 150 ml dry THF under nitrogen atmosphere. Afterwards, 0.25 g (10 mmol) NaH (95%) was slowly added while stirring. The stirring was continued for 2 hours. As a result, a first mixture (solution) was obtained.

In a second step 9.60 g (8 mmol) mono-tosylated monomethyl-capped polyethylene glycol dissolved in 200 ml dry THF was added over a period of 40 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: ethyl acetate/hexane, volume ratio: 50:50). As a result, 9.30 g (yield: 98%) of a compound of Formula (a) was obtained. The compound was additionally investigated by NMR and MALDI-TOF-MS measurements.

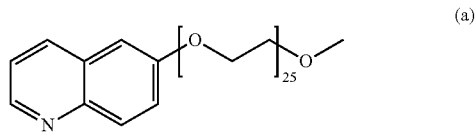

1.2 Acidic Composition Comprising the Compound of Formula (a) and Electrolytic Copper Plating In a first step a plating bath was prepared by mixing (i) copper ions (added as copper (II) sulfate pentahydrate, $CuSO_4 \cdot 5\ H_2O$ (also used in the following examples)) in a total amount of 40 g/L, (ii) compound of Formula (a) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 3 mL/L, and (vi) deionized water.

In a second step electrolytic copper plating was carried out utilizing the acidic composition prepared in the first step. The temperature of the plating bath was 25° C. and a current density of 6.5 mA/cm² was applied for 5.5 seconds. A copper layer was electroplated onto a wafer substrate provided with a copper seed layer and a feature diameter of 48 nm with aspect ratios of approximately 4:1.

Afterwards, in a third step surplus copper was electroplated at a current density of 7.4 mA/cm² for 60 seconds.

In a fourth step the electroplated sample was investigated with SEM (see FIG. 1). FIG. 1 shows copper filled neighboring trenches.

2. Example 2 (According to the Invention, Compound of Formula (b))

2.1 Synthesis

In a first step 5.57 g (38 mmol) 8-hydroxyquinoline was dissolved in 250 mL dry THF under nitrogen atmosphere. Afterwards, 1.00 g (40 mmol) NaH (95%) was slowly added while stirring. The stirring was continued for 2 hours. As a result, a first mixture (solution) was obtained.

In a second step 15.00 g (10 mmol) triply-tosylated glycerin ethoxylate dissolved in 200 mL dry THF was added over a period of 40 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: tetrahydrofuran/hexane, volume ratio: 50:50). As a result, 12.00 g (yield: 85%) of a compound of Formula (b) was obtained. The compound was additionally investigated by NMR and MALDI-TOF-MS measurements.

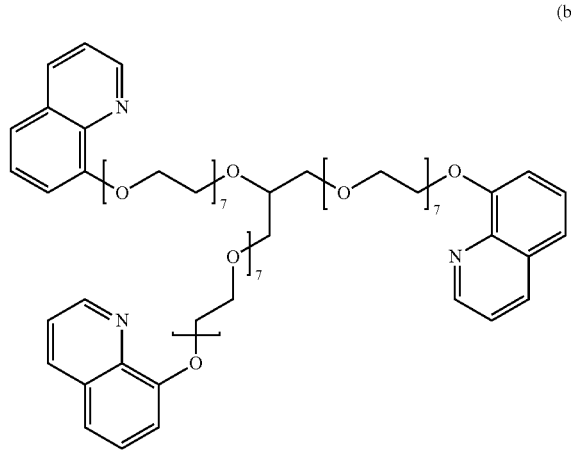

(b)

2.2 Acidic Composition Comprising the Compound of Formula (b) and Electrolytic Copper Plating In a first step a plating bath was prepared by mixing (i) copper ions (added as copper (II) sulfate pentahydrate) in a total amount of 40 g/L, (ii) compound of Formula (b) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 3 mL/L, and (vi) deionized water.

In a second step electrolytic copper plating was carried out utilizing the acidic composition prepared in the first step. The temperature of the plating bath was 25° C. and a current density of 6.5 mA/cm$^2$ was applied for 5.5 seconds. A copper layer was electroplated onto a wafer substrate provided with a copper seed layer and a feature diameter of 48 nm with aspect ratios of approximately 4:1.

Afterwards, in a third step surplus copper was electroplated at a current density of 7.4 mA/cm$^2$ for 60 seconds.

Figure 2:
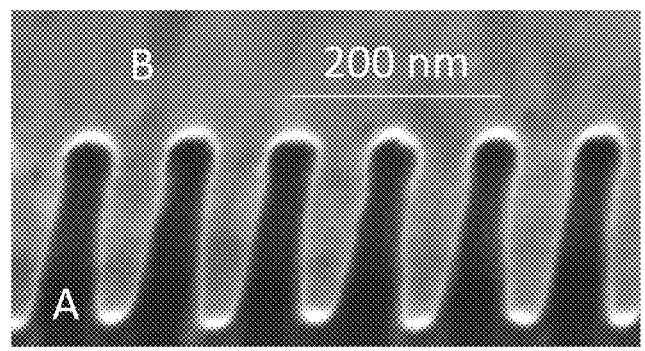
FIG. 2 shows trenches (aspect ratio approximately 4:1) in a substrate (A) filled with copper (B) (an acidic aqueous composition according to the invention comprising the compound of Formula (b) was used).

In a fourth step the electroplated sample was investigated with SEM (see FIG. 2). FIG. 2 shows copper filled neighboring trenches.

3. Example 3 (According to the Invention, Compound of Formula (c))

3.1 Synthesis

In a first step 2.79 g (19 mmol) 6-hydroxyquinoline was dissolved in 150 mL dry THF under nitrogen atmosphere. Afterwards, 0.50 g (20 mmol) NaH (95%) was slowly added while stirring. The stirring was continued for 2 hours. As a result, a first mixture (solution) was obtained.

In a second step 7.50 g (5 mmol) triply-tosylated glycerin ethoxylate dissolved in 200 mL dry THF was added over a period of 40 minutes to the first mixture obtained after the first step. The resulting mixture was stirred at 65° C. for 48 hours under nitrogen atmosphere. While stirring a precipitate was formed.

In a third step the precipitate was removed by filtration and the solvent of the filtrate was removed under reduced pressure; a solvent-free, crude product was obtained.

In a fourth step the solvent-free, crude product obtained after the third step was purified by recycling GPC using tetrahydrofuran as eluent. As a result, 6.60 g (yield: 93%) of a compound of Formula (c) was obtained. The compound was additionally investigated by NMR and MALDI-TOF-MS measurements.

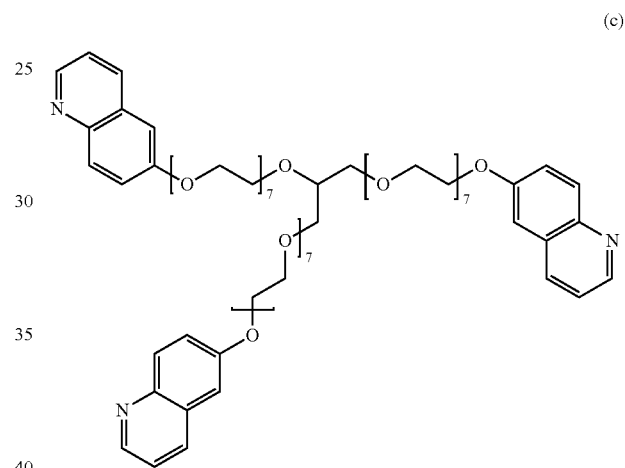

(c)

3.2 Acidic Composition Comprising the Compound of Formula (c) and Electrolytic Copper Plating In a first step a plating bath was prepared by mixing (i) copper ions (added as copper (II) sulfate pentahydrate) in a total amount of 40 g/L, (ii) compound of Formula (c) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 3 mL/L, and (vi) deionized water.

In a second step electrolytic copper plating was carried out utilizing the acidic composition prepared in the first step. The temperature of the plating bath was 25° C. and a current density of 6.5 mA/cm$^2$ was applied for 5.5 seconds. A copper layer was electroplated onto a wafer substrate provided with a copper seed layer and a feature diameter of 48 nm with aspect ratios of approximately 4:1.

Afterwards, in a third step surplus copper was electroplated at a current density of 7.4 mA/cm$^2$ for 60 seconds.

Figure 3:
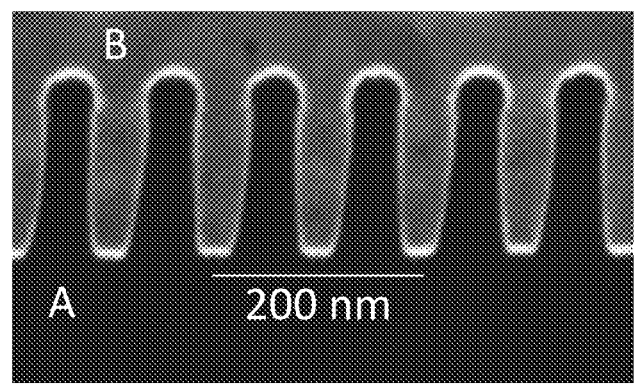
FIG. 3 shows trenches (aspect ratio approximately 4:1) in a substrate (A) filled with copper (B) (an acidic aqueous composition according to the invention comprising the compound of Formula (c) was used).

In a fourth step the electroplated sample was investigated with SEM (see FIG. 3). FIG. 3 shows copper filled neighboring trenches.

4. Example 4 (According to the Invention, Compound of Formula (d))

4.1 Synthesis

In a first step 3.16 g (6 mmol) PEG 500 diglycidyl ether, 0.88 g (6 mmol) 8-hydroxyquinoline, and 0.08 g (0.6 mmol) potassium carbonate were mixed and heated to 60° C. and said temperature was maintained for 24 hours. A first mixture was obtained. Afterwards, 1.04 g (6 mmol) Leucine isopropyl ester was added to the first mixture resulting in a second mixture. The second mixture was stirred at 60° C. for another 72 hours.

In a second step the mixture obtained after the first step was diluted by adding 50 mL THF. The formation of a precipitate (e.g. potassium carbonate) was observed.

In a third step the precipitate was removed by filtration and the solvent of the filtrate was removed under reduced pressure; a solvent-free, crude product was obtained.

In a fourth step the solvent-free, crude product obtained after the third step was purified by recycling GPC (eluent: ethanol). As a result, 3.90 g (yield: 77%) of a compound of Formula (d) was obtained. The compound was additionally investigated by NMR and MALDI-TOF-MS measurements.

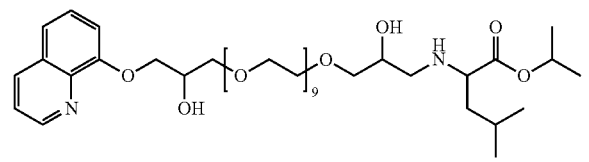

(d)

4.2 Acidic Composition Comprising the Compound of Formula (d) and Electrolytic Copper Plating In a first step a plating bath was prepared by mixing (i) copper ions (added as copper (II) sulfate pentahydrate) in a total amount of 40 g/L, (ii) compound of Formula (d) in a total amount of 0.20 g/L, (iii) sulfuric acid in a total amount of 10 g/L, (iv) chloride ions (added as HCl) in a total amount of 0.050 g/L, (v) an accelerator (trade name: A2X-T) in a total amount of 3 mL/L, and (vi) deionized water.

In a second step electrolytic copper plating was carried out utilizing the acidic composition prepared in the first step. The temperature of the plating bath was 25° C. and a current density of 3.5 mA/cm² was applied for 5.5 seconds. A copper layer was electroplated onto a wafer substrate provided with a copper seed layer and a feature diameter of 48 nm with aspect ratios of approximately 4:1.

Afterwards, in a third step surplus copper was electroplated at a current density of 7.4 mA/cm² for 60 seconds.

Figure 4:
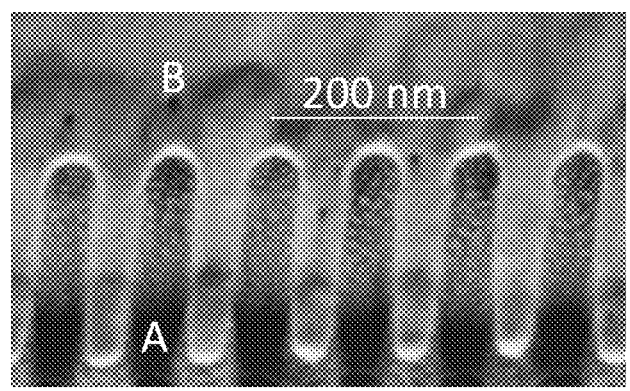
FIG. 4 shows trenches (aspect ratio approximately 4:1) in a substrate (A) filled with copper (B) (an acidic aqueous composition according to the invention comprising the compound of Formula (d) was used).

In a fourth step the electroplated sample was investigated with SEM (see FIG. 4). FIG. 4 shows copper filled neighboring trenches.

5. Example 5 (According to the Invention, Compound of Formula (e))

5.1 Synthesis

In a first step 10.60 g (10 mmol) polyethylene glycol diglycidyl ether was dissolved in 40 mL dry acetonitrile. Afterwards, 2.96 g (20 mmol) 8-hydroxyquinoline and 5.64 g (41 mmol) potassium carbonate were added. As a result, a first mixture was obtained. The first mixture was refluxed for 48 hours at 82° C.

In a second step the mixture obtained after the first step was diluted by adding 50 mL acetonitrile. The formation of a precipitate (e.g. potassium carbonate) was observed.

In a third step the precipitate was removed by filtration and the solvent of the filtrate was removed under reduced pressure. As a result, 11.39 g (yield: 86%) of a compound of Formula (e) was obtained. The compound was additionally investigated by NMR and MALDI-TOF-MS measurements.

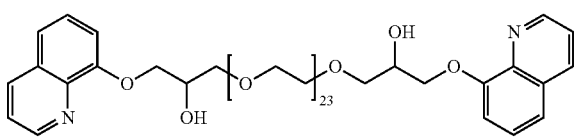

(e)

5.2 Acidic Composition Comprising the Compound of Formula (e) and Electrolytic Copper Plating In a first step a plating bath was prepared by mixing (i) copper ions (added as copper (II) sulfate pentahydrate) in a total amount of 55 g/L, (ii) compound of Formula (e) in a total amount of 0.040 g/L, (iii) sulfuric acid in a total amount of 50 g/L, (iv) chloride ions (added as HCl) in a total amount of 0.050 g/L, (v) SPS (Bis-(sodium sulfopropyl)-disulfide) as an accelerator in a total amount of 2 mL/L, and (vi) deionized water.

In a second step electrolytic copper plating was carried out utilizing the acidic composition prepared in the first step. The temperature of the plating bath was 25° C. and a current density of 2 mA/cm² was applied for 30 minutes. A copper layer was electroplated onto a wafer substrate provided with a copper seed layer and TSV feature dimensions of 5×50 µm (aspect ratio of approximately 10:1).

Figure 5:
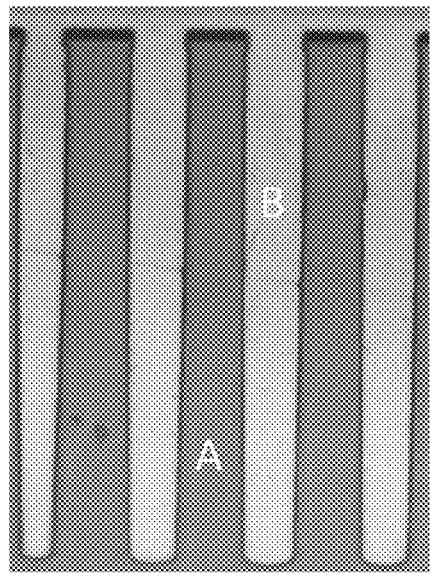
FIG. 5 shows trenches (aspect ratio approximately 10:1, diameter approximately 5 μm) in a substrate (A) filled with copper (B) (an acidic aqueous composition according to the invention comprising the compound of Formula (e) was used).

In a third step the electroplated sample was investigated with optical microscopy (see FIG. 5). FIG. 5 shows copper filled neighboring trenches.

6. Example 6 (According to the Invention, Compound of Formula (f))

6.1 Synthesis

In a first step 2.34 g 6-hydroxyquinoline (16 mmol) was dissolved in 150 ml dry THF under nitrogen atmosphere. Afterwards, 0.43 g (17 mmol) NaH (95%) was slowly added while stirring. The stirring was continued for 2 hours. As a result, a first mixture (solution) was obtained.

In a second step 15.0 g (11 mmol) mono-tosylated mono-lauryl-capped polyethylene glycol dissolved in 250 ml dry THF was added over a period of 60 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: ethyl acetate/hexane, volume ratio: 50:50). As a result, 14.1 g (yield 96%) of a compound of Formula (f) was obtained. The compound was additionally investigated by NMR and MALDI-TOF-MS measurements.

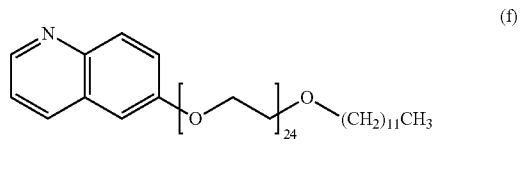

6.2 Acidic Composition Comprising the Compound of Formula (f) and Electrolytic Copper Plating In a first step a plating bath was prepared by mixing (i) copper ions (added as copper (II) sulfate) in a total amount of 60 g/L, (ii) compound of Formula (f) in a total amount of 0.010 g/L, (iii) sulfuric acid in a total amount of 50 g/L, (iv) chloride ions (added as HCl) in a total amount of 0.045 g/L, (v) SPS as a first accelerator in a total amount of 2 mL/L, (vi) deionized water, and (vii) PEG (polyethylene glycol) in a total amount of 0.10 g/L. PEG is an additionally "suppressor" or "carrier" (see in the text above). However, additional PEG does neither negatively affect the filling qualities nor the overpotential obtained in the respective plating bath (corresponding experiments have been carried out for compounds (b), (c) and (i), showing the same effect that neither the filling quality nor the overpotential is negatively affected). Instead, the compound of formula (f) leads to desirable results.

In a second step electrolytic copper plating was carried out utilizing the acidic composition prepared in the first step. A current density of 15 mA/cm$^2$ was applied for 36 minutes. A copper layer was electroplated onto a PCB substrate provided with a copper seed layer and feature dimensions of 100×75 μm.

Figure 6:
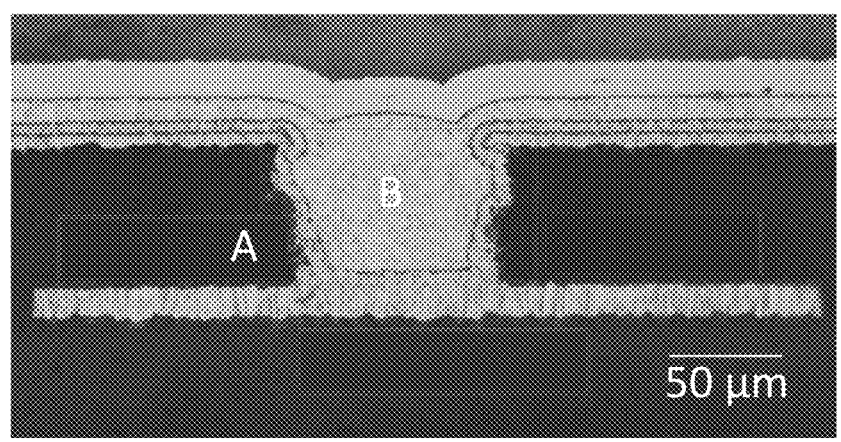
FIG. 6 shows a via (aspect ratio approximately 1:1) in a substrate (A) filled with copper (B) (an acidic aqueous composition according to the invention comprising the compound of Formula (f) was used).

In a third step the electroplated sample was investigated with optical microscopy (see FIG. 6). FIG. 6 shows a via which is uniformly filled with copper.

7. Example 7 (According to the Invention, Compound of Formula (g))

7.1 Synthesis

In a first step 4.33 g 8-hydroxyquinoline (30 mmol) was dissolved in 150 ml dry THF under nitrogen atmosphere. Afterwards, 0.84 g (32 mmol) NaH (95%) was slowly added while stirring. The stirring was continued for 2 hours. As a result, a first mixture (solution) was obtained.

In a second step 16.4 g (12 mmol) di-tosylated polyethylene glycol dissolved in 200 ml dry THF was added over a period of 40 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: ethyl acetate/hexane, volume ratio: 50:50). As a result, 13.0 g (yield: 87%) of a compound of Formula (g) was obtained. The compound was additionally investigated by NMR and MALDI-TOF-MS measurements.

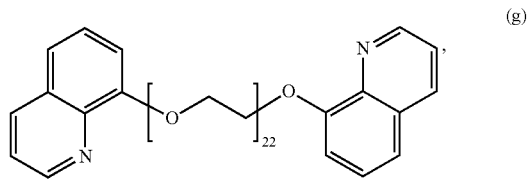

7.2 Acidic Composition Comprising the Compound of Formula (g) and Electrolytic Copper Plating In a first step a plating bath was prepared by mixing (i) copper ions (added as copper (II) sulfate) in a total amount of 40 g/L, (ii) compound of Formula (g) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 4.3 mL/L, and (vi) deionized water.

In a second step electrolytic copper plating was carried out utilizing the acidic composition prepared in the first step. The temperature of the plating bath was 25° C. and a current density of 6.5 mA/cm$^2$ was applied for 5.5 seconds. A copper layer was electroplated onto a wafer substrate provided with a copper seed layer and a feature diameter of 48 nm with aspect ratios of approximately 4:1.

Afterwards, in a third step surplus copper was electroplated at a current density of 7.4 mA/cm$^2$ for 60 seconds.

Figure 7:
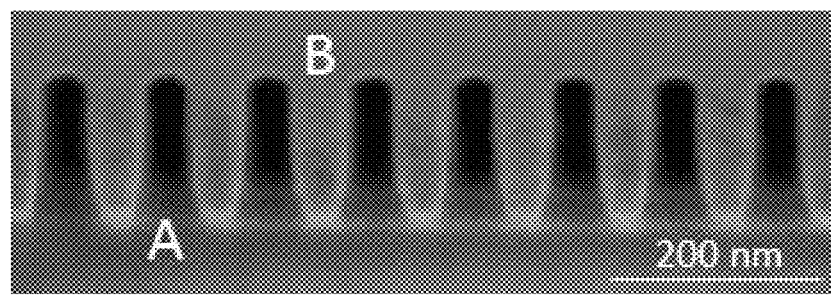
FIG. 7 shows trenches (48 nm, aspect ratio approximately 4:1) in a substrate (A) filled with copper (B) (an acidic aqueous composition according to the invention comprising the compound of Formula (g) was used).

In a fourth step the electroplated sample was investigated with SEM (see FIG. 7). FIG. 7 shows copper filled neighboring trenches.

8. Example 8 (According to the Invention, Compound of Formula (h))

8.1 Synthesis

In a first step 1.60 g 8-hydroxyquinoline (11 mmol) was dissolved in 150 ml dry THF under nitrogen atmosphere. Afterwards, 0.30 g (12 mmol) NaH (95%) was slowly added while stirring. The stirring was continued for 2 hours. As a result, a first mixture (solution) was obtained.

In a second step 12.50 g (5 mmol) di-tosylated polyethylene glycol dissolved in 150 ml dry THF was added over a period of 40 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: ethyl acetate/hexane, volume ratio: 50:50). As a result, 9.0 g (yield: 74%) of a compound of Formula (h) was obtained. The compound was additionally investigated by NMR and MALDI-TOF-MS measurements.

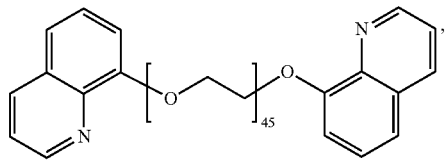

(h)

8.2 Acidic Composition Comprising the Compound of Formula (h) and Electrolytic Copper Plating In a first step a plating bath was prepared by mixing (i) copper ions (added as copper (II) sulfate) in a total amount of 40 g/L, (ii) compound of Formula (h) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 4.3 mL/L, and (vi) deionized water.

In a second step electrolytic copper plating was carried out utilizing the acidic composition prepared in the first step. The temperature of the plating bath was 25° C. and a current density of 6.5 mA/cm$^2$ was applied for 5.5 seconds. A copper layer was electroplated onto a wafer substrate provided with a copper seed layer and a feature diameter of 28 nm with aspect ratios of approximately 4:1.

Afterwards, in a third step surplus copper was electroplated at a current density of 7.4 mA/cm$^2$ for 60 seconds.

Figure 8:
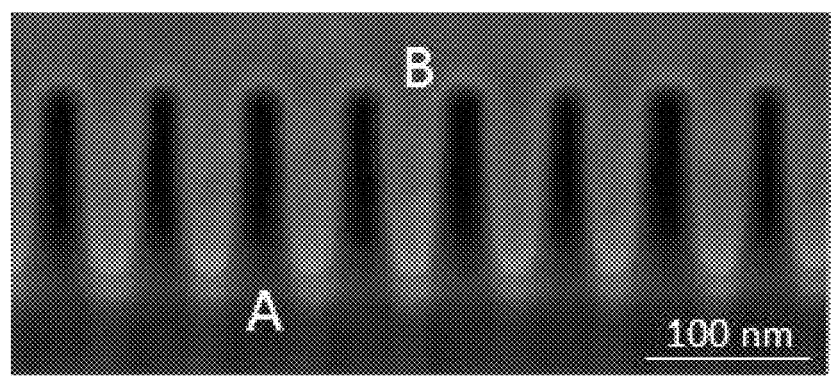
FIG. 8 shows trenches (28 nm, aspect ratio approximately 4:1) in a substrate (A) filled with copper (B) (an acidic aqueous composition according to the invention comprising the compound of Formula (h) was used).

In a fourth step the electroplated sample was investigated with SEM (see FIG. 8). FIG. 8 shows copper filled neighboring trenches.

9. Example 9 (According to the Invention, Compound of Formula (i))

9.1 Synthesis

In a first step 1.27 g 8-hydroxyquinoline (9 mmol) was dissolved in 150 ml dry THF under nitrogen atmosphere. Afterwards, 0.25 g (10 mmol) NaH (95%) was slowly added while stirring. The stirring was continued for 2 hours. As a result, a first mixture (solution) was obtained.

In a second step 10.0 g (4 mmol) di-tosylated poly(ethylene glycol)-b-poly(propylene glycol)-b-poly(ethylene glycol) block copolymer dissolved in 150 ml dry THF was added over a period of 40 minutes to the first mixture obtained after the first step. The resulting mixture was stirred at 65° C. for 48 hours under nitrogen atmosphere.

In a third step the solvent of the mixture obtained after the second step was removed using a rotary evaporator; a solvent-free, crude product was obtained.

In a fourth step the solvent-free, crude product obtained after the third step was purified by column chromatography (eluent: ethyl acetate/hexane, volume ratio: 50:50). As a result, 7.6 g (yield: 78%) of a compound of Formula (i) was obtained. The compound was additionally investigated by NMR and MALDI-TOF-MS measurements.

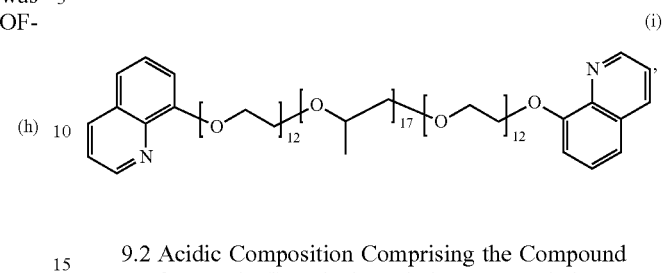

(i)

9.2 Acidic Composition Comprising the Compound of Formula (i) and Electrolytic Copper Plating In a first step a plating bath was prepared by mixing (i) copper ions (added as copper (II) sulfate) in a total amount of 40 g/L, (ii) compound of Formula (i) in a total amount of 0.10 g/L, (iii) sulfuric acid in a total amount of 10 g/L, (iv) chloride ions (added as HCl) in a total amount of 0.050 g/L, (v) an accelerator (trade name: A2X-T) in a total amount of 4.3 mL/L, and (vi) deionized water.

In a second step electrolytic copper plating was carried out utilizing the acidic composition prepared in the first step. The temperature of the plating bath was 25° C. and a current density of 6.5 mA/cm$^2$ was applied for 5.5 seconds. A copper layer was electroplated onto a wafer substrate provided with a copper seed layer and a feature diameter of 28 nm with aspect ratios of approximately 4:1.

Afterwards, in a third step surplus copper was electroplated at a current density of 7.4 mA/cm$^2$ for 60 seconds.

Figure 9:
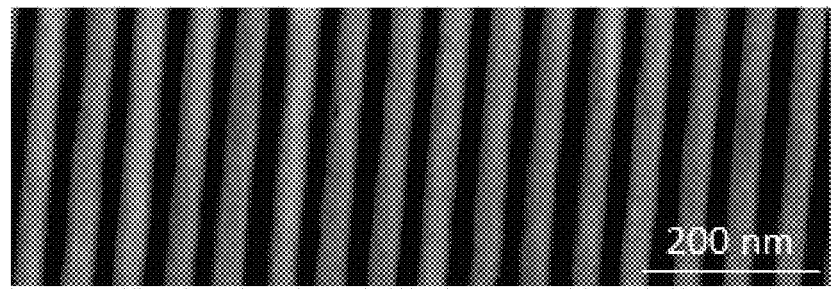
FIG. 9 shows slope cut trenches (28 nm in width, slope 5 to 15 degrees, aspect ratio approximately 4:1) in a substrate (dark lines) filled with copper (light lines) (an acidic aqueous composition according to the invention comprising the compound of Formula (i) was used).

In a fourth step the electroplated sample was investigated with SEM (see FIG. 9). FIG. 9 shows copper filled neighboring trenches.

Table 1a and 1b, respectively, provides a summary of the structural elements of compounds (a) to (i).

10. Example 10 (Comparative Example, not According to the Invention)

In the acidic aqueous comparison composition according to Example 10 (not according to the invention) PEG 3000 was used instead of a compound of component (ii). PEG 3000 is a common additive in respective compositions and is commercially available.

In a first step the comparison composition was prepared by mixing (i) copper ions in a total amount of 40 g/L, (ii) PEG 3000 in a total amount of 0.15 g/L, (iii) sulfuric acid in a total amount of 10 g/L, (iv) chloride ions (added as HCl) in a total amount of 0.050 g/L, (v) an accelerator in a total amount of 12 ml/L, (vi) a carrier in a total amount of 1 ml/L, and (vii) deionized water.

In a second step electrolytic copper plating was carried out utilizing the acidic aqueous comparison composition prepared in the first step. The following plating profile was used: 2 mA/cm$^2$ for 65 minutes; 2.5 mA/cm$^2$ for 15 minutes; 6 mA/cm$^2$ for 7 minutes; and 9.0 mA/cm$^2$ for 3 minutes. A copper layer was electroplated onto a substrate provided with a copper seed layer and feature dimensions of 10×100 μm (aspect ratio of approximately 10:1).

Figure 10:
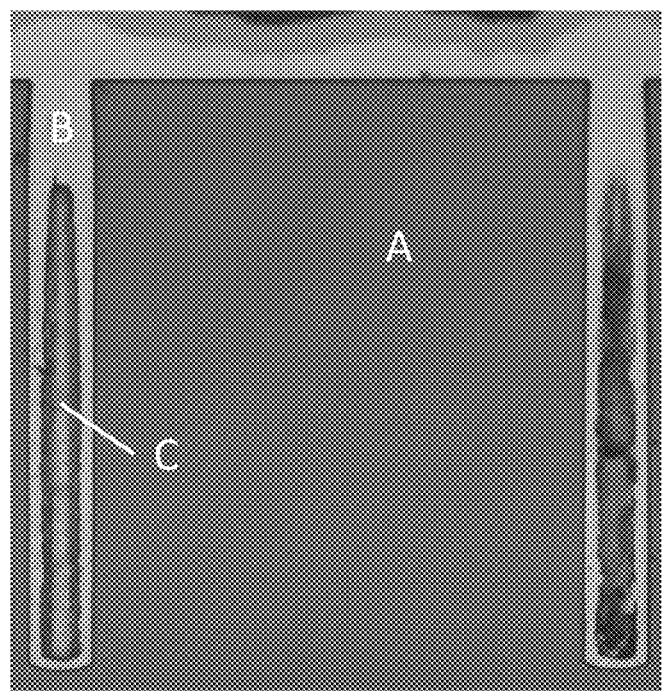
FIG. 10 shows trenches (aspect ratio approximately 10:1, diameter approximately 10 μm) in a substrate (A) filled with copper (B) (an acidic aqueous composition not according to the invention comprising PEG 3000 was used); the trenches clearly comprise large voids (C).

In a third step the electroplated comparative sample was investigated with optical microscopy (see FIG. 10). FIG. 10 shows two trenches comprising huge voids (C).

In each example, the pH in of the acidic composition was significantly below 3, typically below 2.

TABLE 1a summary of structural elements in compounds (a) to (i) (compounds of Formula (Ia)):

| (I)* | $A^1$ | a | x | $B^1$ | $D^1$ | o | $R^1$ | n | p | $R^2$ | s | $R^4$ | $R^5$ | q | $R^3$ | y | $B^2$ | $D^2$ | b | $A^2$ |
|---|---|---|---|---|---|---|---|---|---|---|---|---|---|---|---|---|---|---|---|---|
| (a) | quinoline | 0 | 0 | — | O | 25 | H | 1 | 0 | — | 0 | — | — | 0 | — | 0 | — | O | 0 | —CH$_3$ |
| (b) | quinoline | 0 | 0 | — | O | 7 | H | 1 | 0 | — | 1 | (IIa)** | H | 7 | H | 0 | — | O | 0 | quinoline |
| (c) | quinoline | 0 | 0 | — | O | 7 | H | 1 | 0 | — | 1 | (IIa)** | H | 7 | H | 0 | — | O | 0 | quinoline |
| (d) | quinoline | 0 | 1 | O | O | 9 | H | 1 | 0 | — | 0 | — | — | 0 | — | 1 | NH | O | 0 | isopropyl ester of leucine |
| (e) | quinoline | 0 | 1 | O | O | 23 | H | 1 | 0 | — | 0 | — | — | 0 | — | 1 | O | O | 0 | quinoline |
| (f) | quinoline | 0 | 0 | — | O | 24 | H | 1 | 0 | — | 0 | — | — | 0 | — | 0 | — | O | 0 | —(CH$_2$)$_{11}$CH$_3$ |
| (g) | quinoline | 0 | 0 | — | O | 22 | H | 1 | 0 | — | 0 | — | — | 0 | — | 0 | — | O | 0 | quinoline |
| (h) | quinoline | 0 | 0 | — | O | 45 | H | 1 | 0 | — | 0 | — | — | 0 | — | 0 | — | O | 0 | quinoline |
| (i) | quinoline | 0 | 0 | — | O | 12 | H | 1 | 17 | CH$_3$ | 0 | — | — | 12 | H | 0 | — | O | 0 | quinoline |

*refers to the specific compound synthesized according to section "Examples"
**refers to a moiety of Formula (IIa) (see Table 1b)
"—" means: not present in the structure

TABLE 1b

| (I)* | moiety | t | R⁶ | z | D³ | B³ | c | A³ |
|---|---|---|---|---|---|---|---|---|
| (b) | $R^4$ | 7 | H | 0 | O | — | 0 | 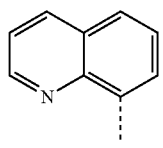 |
| (c) | $R^4$ | 7 | H | 0 | O | — | 0 | 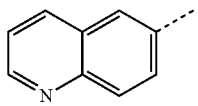 |

B. Experiments and Results (Overpotential)

B.1 Experimental Setup

The overpotential of each compound (a) to (i) (and further compounds not shown here) was determined in a standard injection experiment.

An aqueous solution was provided containing 50 g/L copper sulfate, 50 g/L sulfuric acid, and 50 ppm chloride ions (added as HCl). The respective compound was added in a concentration of 100 ppm to said aqueous solution. The reference compound was PEG 3000. Each measurement was carried out at 25° C.

The overpotential obtained with PEG was set as reference (1.00), wherein the overpotential obtained for compounds (a) to (i) was determined relative to the reference (see Table 2 below).

B.2 Results

TABLE 2

| compound | overpotential |
|---|---|
| PEG 3000 | 1.00 |
| (a) | 1.44 |
| (b) | 1.42 |
| (c) | 1.41 |
| (d) | 1.31 |
| (e) | 1.21 |
| (f) | 1.43 |
| (g) | 1.49 |
| (h) | 1.45 |
| (i) | 1.48 |

As shown in Table 2, the overpotential generated by compounds (a) to (i) is significantly increased compared to the overpotential generated by PEG 3000. PEG 3000 is a commonly used compound in the art.

The invention claimed is:

1. A composition comprising one or a mixture of two or more quinoline-polyethylene glycol containing compound, each quinoline-polyethylene glycol containing compound comprising:
   one to three quinoline group and
   one or more polyethylene glycol group,
wherein, in each said quinoline-polyethylene glycol containing compound, one to three of said one to three quinoline group is connected via one or more oxygen atom of said one or more polyethylene glycol group via carbon 6 or carbon 8 of said one to three quinoline group, wherein the compound is selected from the group consisting of:

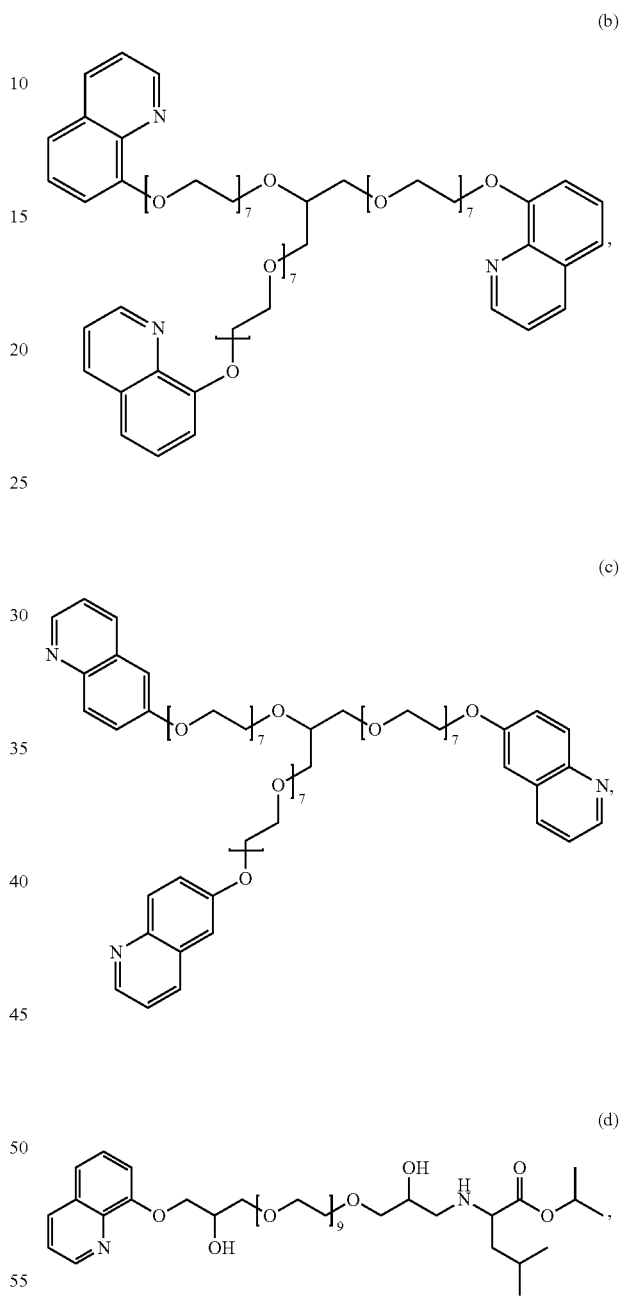

-continued
(f) 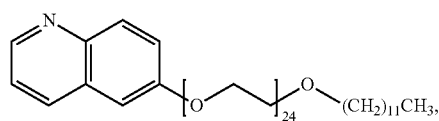
(g) 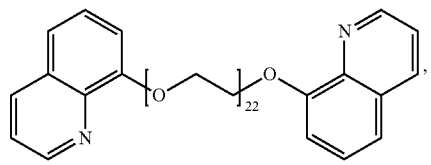
(h) 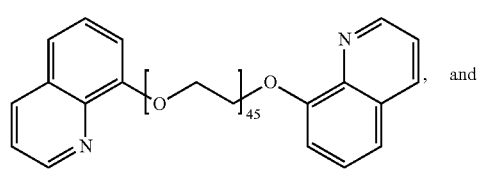, and
(i) 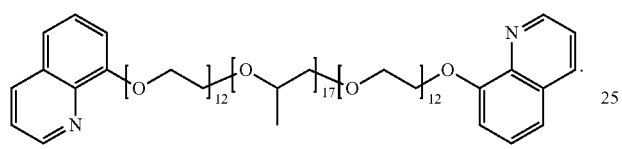
2. One or a mixture of two or more compound according to claim 1 wherein the compound comprises:
(b)
* * * * *